(12) United States Patent
Vandali et al.

(10) Patent No.: US 8,023,673 B2
(45) Date of Patent: Sep. 20, 2011

(54) PITCH PERCEPTION IN AN AUDITORY PROSTHESIS

(75) Inventors: Andrew Vandali, Lane Cove (AU);
Richard Van Hoesel, Lane Cove (AU);
Peter Seligman, Lane Cove (AU)

(73) Assignee: Hearworks Pty. Limited, East Melbourne, VIC (AU)

( * ) Notice: Subject to any disclaimer, the term of this patent is extended or adjusted under 35 U.S.C. 154(b) by 1753 days.

(21) Appl. No.: 11/236,510

(22) Filed: Sep. 28, 2005

(65) Prior Publication Data

US 2006/0080087 A1  Apr. 13, 2006

Related U.S. Application Data

(63) Continuation-in-part of application No. 11/025,930, filed on Jan. 3, 2005, now Pat. No. 7,561,709.

(60) Provisional application No. 60/613,230, filed on Sep. 28, 2004, provisional application No. 60/613,229, filed on Sep. 28, 2004.

(51) Int. Cl.
*H04R 25/00* (2006.01)

(52) U.S. Cl. ............... 381/320; 381/312; 381/321

(58) Field of Classification Search .......... 381/3, 7, 381/61, 104, 106, 107, 312, 320, 321; 600/559; 607/56, 57; 704/200.1, 205, 225, 226
See application file for complete search history.

(56) References Cited

U.S. PATENT DOCUMENTS 7,072,717 B1 * 7/2006 Wolf et al. .................. 607/57
7,444,280 B2 * 10/2008 Vandali et al. ............. 704/200.1

OTHER PUBLICATIONS

Geurts, et al., "Coding of the fundamental frequency in continuous interleaved sampling processors for cochlear implants," *J. Accoust. Soc. Am.* 109 (2), Feb. 2001.
Green, et al., "Enhancing temporal cues to voice pitch in continuous interleaved sampling cochlear implants," *J. Acoust. Coc. Am.* 116 (4), Pt 1, Oct. 2004.
Vandali, Andrew E., "Pitch ranking ability of cochlear implant recipients: A comparison of sound-processing strategies," *J. Acoust. Soc. Am.* 117 (5), May 2005.

* cited by examiner

*Primary Examiner* — Huyen D Le
(74) *Attorney, Agent, or Firm* — Kilpatrick Townsend & Stockton LLP

(57) ABSTRACT

A sound processing process, device and software are disclosed which seek to improve pitch perception, with particular application to auditory prostheses. After input sound signals are processed into channels, an algorithm is applied to selectively increase the modulation depth of the envelope signals. In certain embodiments, the channelized signals are adjusted in timing so as to align the phase of modulated envelope signals in different channels. This results in provision of synchronous (phase aligned) modulation periodicity across channels and hence less pitch ambiguity for listeners to the processed signal, or for application of the signal to hearing prostheses such as cochlear implants. In some embodiments, a broadband envelope signal is used to modulate the level of the narrow band channel signals, so that voicing frequency modulation information in the broadband envelope signal is provided in all narrow band channel signals and the phase of modulated signals in the channels are aligned. A preferred form uses an envelope signal which is modified to increase its modulation depth, and is normalized so as to allow for modulation of the channel signals.

15 Claims, 25 Drawing Sheets

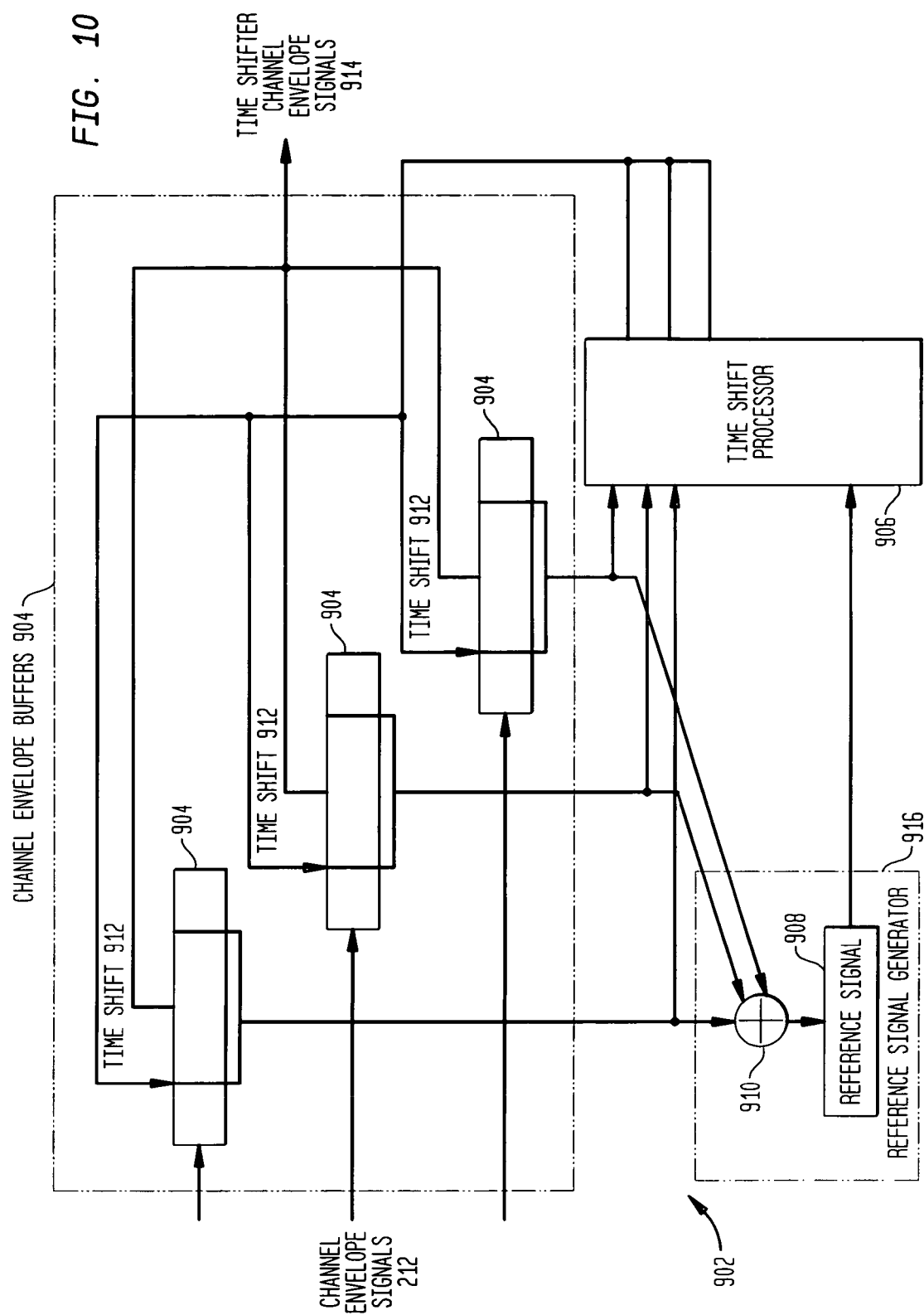

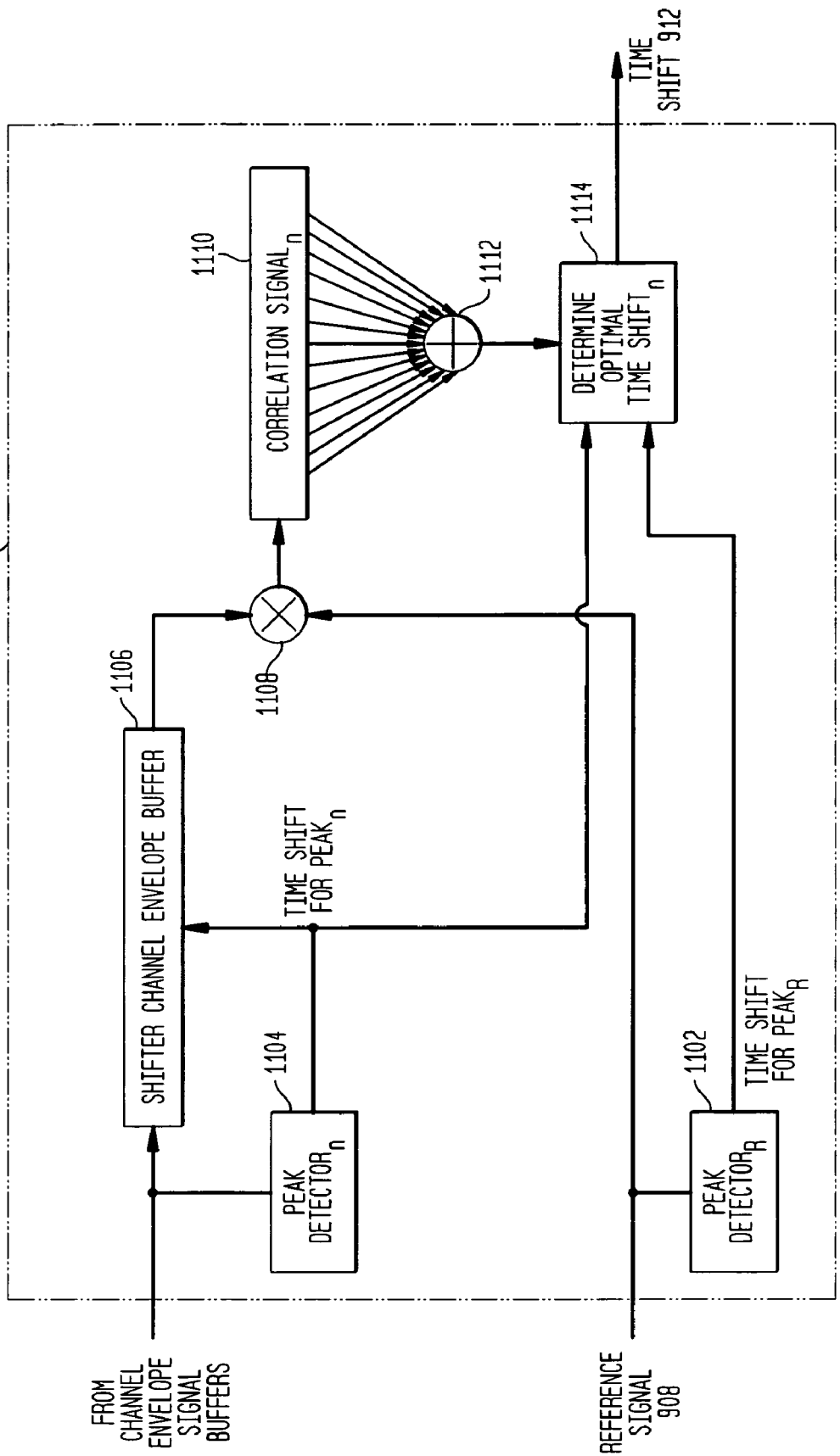

HPF ENVLOPE

SUMMED HPF AND LPF ENVELOPE

NORMALIZED ENVELOPE

NARROW-BAND CHANNEL SIGNAL

NARROW-BAND CHANNEL ENVELOPE
1307

MODULATED CHANNEL SIGNAL
1314

FIG. 23 CAPTURED ELECTRODOGRAM FROM THE ACE STRATEGY FOR THE UTTERANCE "DOG" SPOKEN BY A FEMALE SPEAKER OF F0 ~190 Hz

CAPTURED ELECTRODOGRAM FROM THE MEM STRATEGY FOR THE UTTERANCE "DOG" SPOKEN BY A FEMALE SPEAKER OF F0~190 Hz Env K=4

CAPTURED ELECTRODOGRAM FROM THE MEM STRATEGY FOR THE UTTERANCE "DOG" SPOKEN BY A FEMALE SPEAKER OF F0~190 Hz Env K=1

NARROW-BAND CHANNEL ENVELOPE

MODULATED CHANNEL SIGNAL
1314

NORMALIZED ENVELOPE

INVERSE MODULATION DEPTH

ADJUSTED NORMALIZED ENVELOPE

MODULATED CHANNEL SIGNAL

ADJUSTED NORMALIZED ENVELOPE

MODULATED CHANNEL SIGNAL

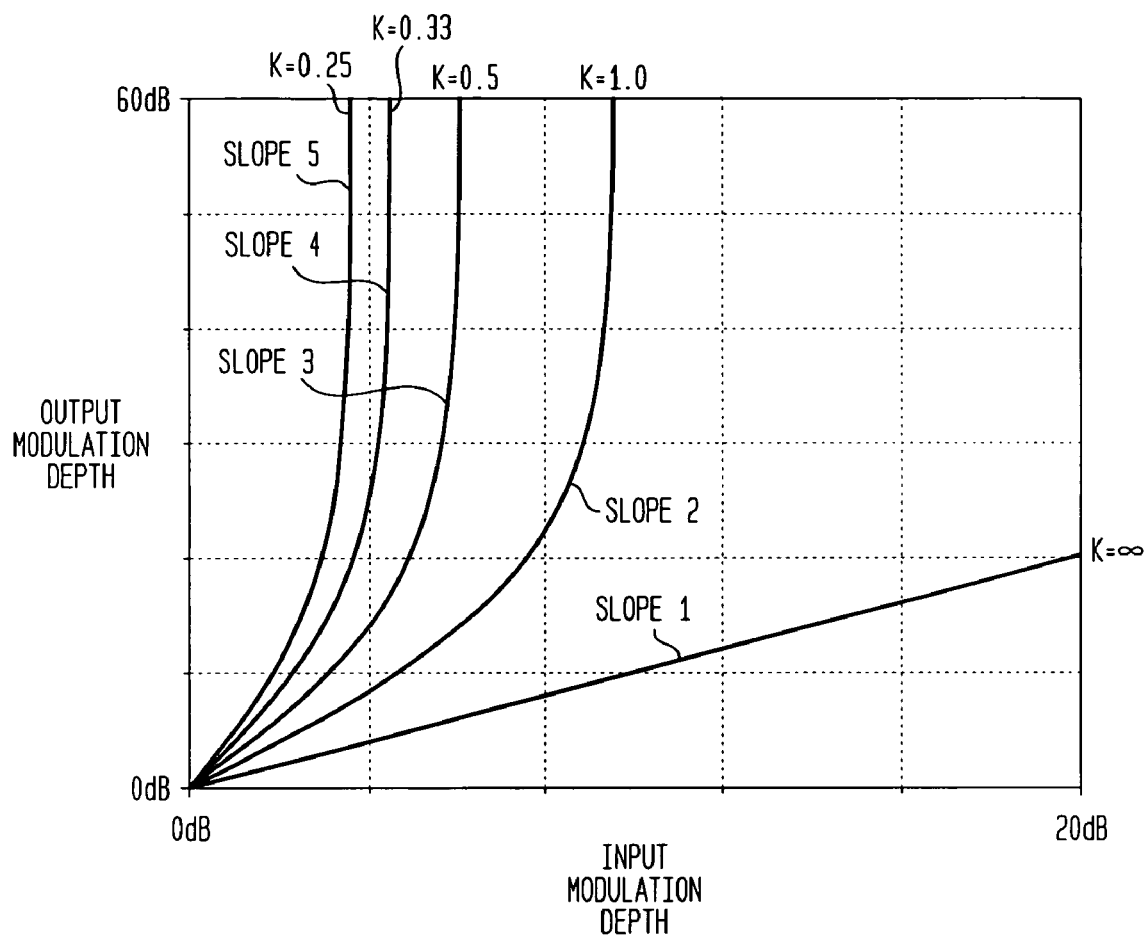

PITCH PERCEPTION IN AN AUDITORY PROSTHESIS

CROSS-REFERENCE TO RELATED APPLICATIONS

The present application is a continuation-in-part application of U.S. patent application Ser. No. 11/025,930, now U.S. Pat. No. 7,561,709 filed Jan. 3, 2005, entitled "Modulation Depth Enhancement for Tone Perception, naming as inventors Andrew Vandali and Richard Van Hoesel, which claims the priority of AU Provisional Application 2003907206, filed on Dec. 31, 2003. The present application claims priority from U.S. Provisional Patent Application 60/613,230, filed Sep. 28, 2004, entitled "Phase Alignment of Amplitude Sound Signals," naming as inventors Andrew Vandali and Richard Van Hoesel. The present application claims priority from U.S. Provisional Patent Application 60/613,229, filed Sep. 28, 2004, entitled "Multi-Channel Envelope Modulation," naming as inventors Andrew Vandali, Richard Van Hoesel, and Peter Seligman. The above applications are hereby incorporated by reference herein in their entirety.

BACKGROUND

1. Field of the Invention

The present invention relates generally to auditory prostheses and, more particularly, to pitch perception in an auditory prosthesis.

2. Related Art

Voice pitch information can play an important role in speech perception as it provides cues to linguistic features such as intonation (question—statement contrast) and word emphasis (Highnam, & Morris 1987; Nooteboom, 1997; Wells, Peppe, & Vance, 1995). Voice pitch information also may make a significant contribution to paralinguistic features such as speaker identification and the emotional state of the speaker (Abberton & Fourcin, 1978; Liberman, & Michaels, 1962) and segregation of concurrent speakers (Brokx, & Nooteboom, 1982).

Most importantly, voice pitch information is crucial for perception of tonal languages, such as Mandarin and Cantonese, where a change in fundamental voicing frequency within the same phonemic segment causes a change in lexical meaning (Lee et. al., 2002; Ciocca et. al., 2002; Barry & Blamey, 2002). Pitch information is also of importance to the appreciation of music wherein the fundamental frequency and its harmonics govern the pitch of the signal (Moore, 1995; McKay & McDermott, 1997; Pijl 1995).

Various speech processing strategies have been developed for processing sound signals for use in stimulating auditory prostheses, such as Cochlear™ prostheses and hearing aids. The multi-peak strategy (Seligman, Dowell, & Blarney, 1992; Skinner et. al., 1991) focused particularly on coding of aspects of speech, such as formants and the fundamental voicing frequency. For this strategy voice pitch information was predominantly coded in the electrical stimulation rate. Other conventional strategies relied more on general channelization of the sound signal, such as the Spectral Maxima Sound Processor (SMSP) strategy, which is described in greater detail in Australian Patent No. 657959 and U.S. Pat. No. 5,597,390, both of which are hereby incorporated by reference herein. For this strategy voice pitch information (for a voicing frequency below approximately 200 Hz) is generally coded in the envelope signals of each channel by amplitude modulation at a frequency equal to or related to the voicing frequency.

SUMMARY

In one aspect of the invention, a method for processing a sound signal having a fundamental frequency is disclosed. The method comprises: processing the sound signal to produce channel signals in spaced frequency channels; determining an envelope signal for each of a plurality of the channel signals; and modulating the envelope signals in each channel with at least one broadband envelope signal derived from the input sound signal, such that the phase of modulated signals in the narrow band channels are synchronized.

In another aspect of the invention, a machine readable medium storing instructions that, when executed by a computer system, causes the computer system to perform a set of operations comprising the above operations.

In a further aspect of the invention, a speech processing unit for processing a sound signal is disclosed. The speech processing unit comprises: a filter bank configured to process the sound signal to generate envelope signals in each of a plurality of spaced frequency channels; a broadband envelope detector configured to measure the envelope of at least one broadband signal; and a channel modulation module that uses the at least one broadband envelope signal to modulate the channel envelope signals to generate modulated envelope signals.

In a still further aspect of the present invention, an auditory prosthesis for generating a therapeutic output representative of a received sound signal is disclosed. The auditory prosthesis comprises a speech processing unit configured to operations noted above. In one embodiment, the speech processing unit comprises the elements noted above.

In another aspect of the invention, a speech processing unit for processing a sound signal is disclosed. The speech processing unit comprises: means for processing the sound signal to produce channel signals in spaced frequency channels; means for determining an envelope signal for each of a plurality of the channel signals; and means for modulating the envelope signals with at least one broadband envelope signal containing modulation information related to the fundamental frequency of the sound signal such that the modulated envelope signals have synchronized phases and contain the modulation information.

BRIEF DESCRIPTION OF THE DRAWINGS

Illustrative embodiments of the present invention will now be described with reference to the accompanying drawings, in which:

FIG. 10 is a schematic representation of the phase alignment algorithm;

FIG. 11 is a schematic representation of the time shift processing system;

FIG. 35 depicts the input/output function for modulation depth plotted on log dB scales for embodiments of the MEM strategy aspect of the present invention.

DETAILED DESCRIPTION

Table of Contents

Figure 1:
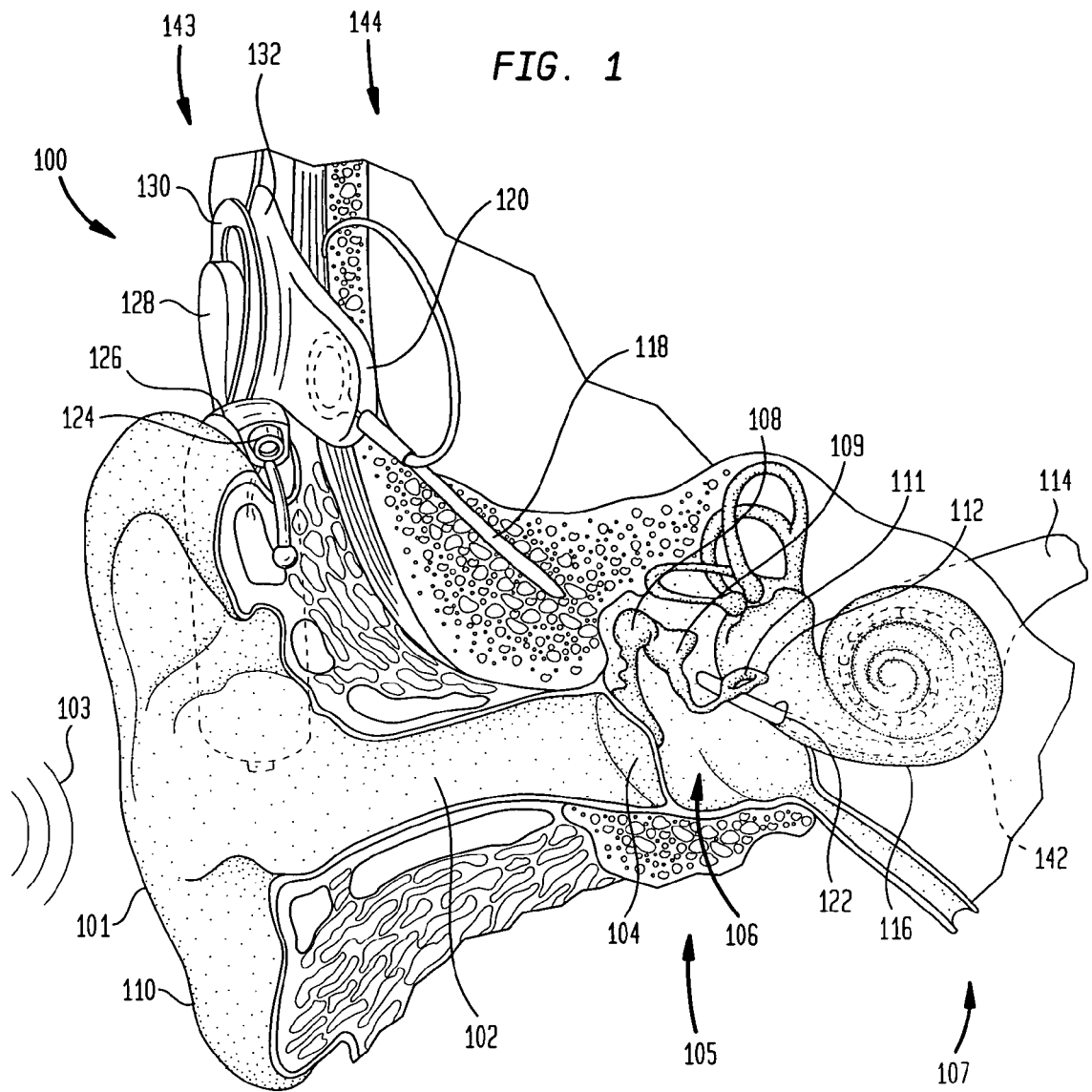
FIG. 1 is a perspective view of an exemplary prosthetic hearing device, a cochlear implant, in which embodiments of the present invention may be advantageously implemented.

A. Introduction
B. Exemplary Auditory Prosthesis
C. Modulation Depth Enhancement
D. Envelope Signal Phase Alignment
E. Multi-Channel Envelope Modulation
F. References
G. Closing A. Introduction Experiments conducted with recipients of cochlear implants have indicated that the frequency of amplitude-modulated electrical signals can be reliably detected when the modulation depth is sufficiently deep (McKay, McDermott, & Clark, 1994; and work in progress by the present inventors). Results among recipients varied but showed consistent identification for depths of at least 6 to 12 dB, and up to 30 dB. Channelization of the sound signal, as is done by most speech coding strategies today, provides an estimate of the narrow-band envelope signal in each band-pass filter channel. For voiced speech signals, voicing pitch (periodicity) information will be represented in the narrow-band envelope signals as an amplitude-modulated signal with a frequency equal to or related to the voicing frequency.

From prior studies of pitch perception, the inventors also concluded that current channelization-based speech processing strategies, in which a sound signal is processed within defined frequency channels, may not provide adequate coding for identification of the modulation frequency in the channel envelope signals. Certain embodiments of the present invention implement what is generally and collectively referred to herein as Modulation Depth Enhancement (MDE) strategies to improve voice perception. In such embodiments, a received sound signal is processed to produce a set of signals in spaced frequency channels. Then, for at least some frequency channel signals, when the ratio of the peak level to the trough level of the envelope signal in that channel ("modulation depth" herein) over some finite time period is less than a threshold value, the modulation depth is increased by, for example, some constant function, in a smoothly varying fashion, or by different functions at defined breakpoints. This expansion may provide improved identification of the modulation frequency and thus the voicing or musical pitch of the sound signal.

The amplitude-modulated narrow-band envelope signals may differ in phase between channels. Experimental findings with cochlear implant recipients have shown that phase differences between modulation signals in neighboring channels (for example, spacing of 3 to 5 electrode channels, or spacing of approximately 2 to 4 mm) can compromise identification of modulation frequency due to temporal integration of signals across channels (McKay & McDermott, 1996; and work in progress by the present applicant), and/or spread of the electrical stimulus current field. One aspect of the present invention implements what is generally and collectively referred to herein as Phase Alignment techniques to minimize the phase differences between peaks in amplitude-modulated envelope signals across channels. Such phase alignment may improve modulation frequency perception.

Another aspect of the present invention is generally directed to modulating the narrow band envelope signals in each channel by a broadband envelope signal derived from the input sound signal, such that the phase of modulated signals in the narrow band channels are synchronized. For voiced or periodic signals, the broadband envelope signal contains modulation components related to the fundamental frequency of the input sound signal. In the specific case of speech, this includes the voicing frequency. Consequently, modulation information related to the fundamental frequency is provided on all narrow band channels. Additionally, in certain embodiments, the modulation depth (for voicing frequency components, for example) in the broadband envelope signal is increased, and accordingly the average modulation depth in each channel is generally increased, so that the modulation frequency information may be more reliably perceived by the recipient.

B. Exemplary Auditory Prosthesis

Embodiments of the present invention are described herein primarily in connection with one type of stimulating medical device, an auditory prosthesis. Auditory prostheses include but are not limited to hearing aids, auditory brain stimulators, and Cochlear™ implants (also commonly referred to as Cochlear™ prostheses, Cochlear™ devices, Cochlear™ implant devices, and the like; generally and collectively referred to as "cochlear implants" herein). Cochlear implants use direct electrical stimulation of auditory nerve cells to bypass absent or defective hair cells that normally transduce acoustic vibrations into neural activity. Such devices generally use an electrode array inserted into the scala tympani of the cochlea so that electrodes of the array may differentially activate auditory neurons that normally encode differential pitches of sound. Auditory brain stimulators are used to treat recipients with bilateral degeneration of the auditory nerve. For such recipients, an auditory brain stimulator provides stimulation of the cochlear nucleus in the brainstem, typically with a planar electrode array; that is, an electrode array in which the electrode contacts are disposed on a two dimensional surface that can be positioned proximal to the brainstem. FIG. 1 is a perspective view of an exemplary cochlear implant in which embodiments of the present invention may be implemented, for example, to improve the voice pitch perception of a recipient of the device.

The relevant components of outer ear 101, middle ear 105 and inner ear 107 are described next below. In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to acoustic wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify acoustic wave 103, causing oval window 112 to articulate, or vibrate. Such vibration sets up waves of fluid motion within cochlea 116. Such fluid motion, in turn, activates tiny hair cells (not shown) that line the inside of cochlea 116. Activation of the hair cells causes appropriate nerve impulses to be transferred through the spiral ganglion cells (not shown) and auditory nerve 114 to the brain (not shown), where they are perceived as sound.

Cochlear implant system 100 comprises external component assembly 143 which is directly or indirectly attached to the body of the recipient, and an internal component assembly 144 which is temporarily or permanently implanted in the recipient. External assembly 143 typically comprises microphone 124 for detecting sound, a speech processing unit 126, a power source (not shown), and an external transmitter unit 128. External transmitter unit 128 comprises an external coil 130 and, preferably, a magnet (not shown) secured directly or indirectly to the external coil. Speech processing unit 126 processes the output of microphone 124 that is positioned, in the depicted embodiment, by ear 110 of the recipient. Speech processing unit 126 generates coded signals, referred to herein as a stimulation data signals, which are provided to external transmitter unit 128 via a cable (not shown). Speech processing unit 126 is, in this illustration, constructed and arranged so that it can fit behind outer ear 110. Alternative versions may be worn elsewhere on the recipient's body.

Internal component assembly 144 comprise an internal receiver unit 132, a stimulator unit 120 and an electrode assembly 118. Internal receiver unit 132 comprises an internal transcutaneous transfer coil (not shown), and preferably, a magnet (also not shown) fixed relative to the internal coil. Internal receiver unit 132 and stimulator unit 120 are hermetically sealed within a biocompatible housing. The internal coil receives power and data from external coil 130, as noted above. A cable or lead of electrode assembly 118 extends from stimulator unit 120 to cochlea 116 and terminates in an array 142 of electrodes. Signals generated by stimulator unit 120 are applied by the electrodes of electrode array 142 to cochlear 116, thereby stimulating the auditory nerve 114.

In one embodiment, external coil 130 transmits electrical signals to the internal coil via a radio frequency (RF) link. In such embodiments, the internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 132 may be positioned in a recess of the temporal bone adjacent ear 110 of the recipient.

Further details of the above and other exemplary auditory prostheses in which embodiments of the present invention may be implemented include, but are not limited to, those systems described in U.S. Pat. Nos. 4,532,930, 6,537,200, 6,565,503, 6,575,894 and 6,697,674, which are hereby incorporated by reference herein in their entireties. For example, while cochlear implant system 100 is described as having external components, in alternative embodiments, implant system 100 may be a totally implantable prosthesis. In one exemplary implementation, for example, speech processor 116, including the microphone, speech processor and/or power supply may be implemented as one or more implantable components. In one particular embodiment, speech processor 116 may be contained within the hermetically sealed housing used for stimulator unit 126.

It should also be appreciated that although embodiments of the present invention are described herein in connection with cochlear implant 100, the same or other embodiments of the present invention may be implemented in other tissue-stimulating medical devices as well. Examples of such devices include, but are not limited to, other sensory prosthetic devices, neural prosthetic devices, and functional electrical stimulation (FES) systems. In sensory prostheses, information is collected by electronic sensors and delivered directly to the nervous system by electrical stimulation of pathways in or leading to the parts of the brain that normally process a given sensory modality. Neural prostheses are clinical applications of neural control interfaces whereby information is exchanged between neural and electronic circuits. FES devices are used to directly stimulate tissue having contractile cells to produce a controlled contraction of the same.

Thus, it will be appreciated that the present invention relates to an improvement which is applicable to a wide range of sound processing strategies for auditory prostheses, as well as other applications. Accordingly, the following implementation is not to be taken as limitative of the scope or applicability of the present invention.

Exemplary embodiments of the present invention will be described with reference to a cochlear implant sound processing system. The precise system employed is not critical to the applicability of the present system. The present implementation will be described with reference to its use with the SMSP strategy (McDermott, & Vandali, 1991; McDermott, McKay, & Vandali, 1992), which is similar to the SPEAK strategy (Skinner et. al., 1994; Whitford et. al., 1995) and Advanced Combinational Encoder (ACE) strategy (Vandali et. al., 2000). Note, however that embodiments of the present invention may equally be applied to other speech coding strategies such as the Continuous Interleaved Sampling (CIS) strategy (Wilson et. al., 1991).

C. Modulation Depth Expansion

From the prior studies of pitch perception, the inventors concluded that current channelization-based speech processing strategies in which the sound signal generated by microphone 124 is processed within defined frequency channels, may not provide adequate coding for identification of the modulation frequency of the channel envelope signals. In certain embodiments, a received sound 103 is processed to produce a set of signals in spaced frequency channels. Then, for at least some frequency channel signals, when the ratio of the peak level to the trough level of the envelope signal in that channel ("modulation depth" herein) over some finite time period is less than a threshold value, the modulation depth is increased. The modulation depth may be expanded by, for example, some constant function when it is below a given threshold, in a smoothly varying fashion, or by different functions at defined breakpoints. Alternative parameters could be adjusted, which have the effect of expanding the modulation depth. This expansion may provide improved identification of the modulation frequency and thus the voicing or musical pitch of the sound signal.

It should be appreciated that embodiments of this aspect of the present invention are applicable to processing sound signals for auditory prostheses, including cochlear implants such as the one described above with reference to FIG. 1, and hearing aids, as well as other applications where it may be desirable to improve the perception of voice pitch or musical tone.

Figure 2:
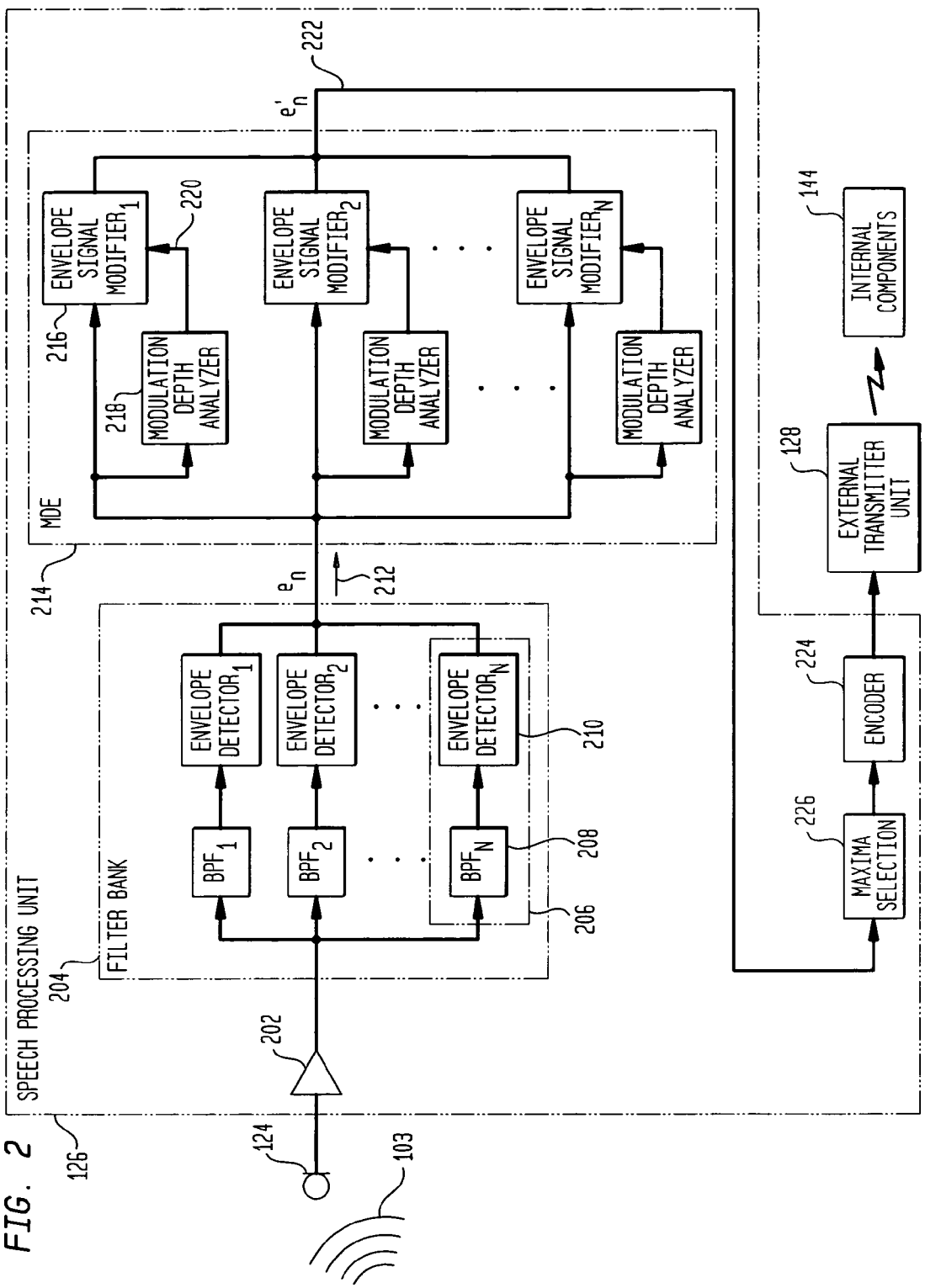
FIG. 2 is a functional block diagram of the speech processing unit illustrated in FIG. 1 which applies signal processing operations to a sound signal in accordance with one embodiment of the present invention.

FIG. 2 is a functional block diagram of one embodiment of the relevant portions of speech processing unit 126 illustrated in FIG. 1. Referring to FIGS. 1 and 2, electrical signals corresponding to sound signals 103 received via a microphone 124 are provided to speech processing unit 126. Speech processing unit 126 comprises a pre-amplifier 202 which amplifies the received sound signals and provides them to a filter bank 204. Filter bank 204 is a bank of N parallel filter channels 206 tuned to adjacent frequencies. In one embodiment, the quantity of parallel filter channels 206 (that is, N) is 16 consistent with the conventional SMSP strategy. It should be understood, however, that in alternative implementations any quantity of filter channels 206 may utilized. In one particular embodiment, filter bank 204 comprises 20 filter channels 206.

Each filter channel 206 comprises a band-pass filter (BPF) 208 and an envelope detector 210. Band-pass filters 208 are typically narrow (approximately 180 Hz) for apical (low-frequency) channels and increase in bandwidth (typically up to 1000 Hz or more) for more basal (higher frequency) channels. Envelope detector 210 provides an estimate of the narrow-band envelope signal in each frequency channel. In one embodiment, envelope detectors 210 effectively comprise a full-wave (quadrature) rectifier followed by a low-pass filter. Envelope detectors 210 typically pass fundamental (modulation) frequency information up to approximately 180 Hz to 400 Hz although for some implementations higher frequencies may be passed.

In certain embodiments, filter bank 204 is implemented using either a Fast Fourier Transform (FFT) or a Finite Impulse Response (FIR) filter bank (which uses complex coefficients). Both implementations effectively perform the band-pass filtering, full-wave (quadrature) rectification and low-pass filtering operations. One implementation of the FFT filter bank embodiment provides a fixed low-pass filter cut-off frequency (for −3 dB gain) of 180 Hz. The complex coefficient FIR filter bank embodiment provides a low-pass filter cut-off frequency equal to the (−3 dB) bandwidth of the band-pass filters. Basal (high frequency) channels can be as wide as 1000 Hz or more and thus an additional second-order low-pass filter (with a cut-off frequency of 400 Hz) can optionally be employed to remove from the envelope signals any frequencies above the fundamental voicing frequency. The advantage of employing the complex coefficient FIR over the FFT filter banks is that higher voicing frequencies can be passed, provided that the band-pass filters are wider than 180 Hz.

Filter bank 204 may be implemented to provide an estimate of the envelope signals in each frequency channel at regular time intervals known as the analysis or update rate. The SMSP strategy conventionally employs a relatively low analysis rate of approximately 250 Hz. However, in this implementation a much higher update rate of approximately 1200 to 1600 Hz is employed so that modulation frequencies of approximately 300 to 400 Hz can be adequately sampled. Such update rates are available with current commercial cochlear implants and speech coding strategies such as ACE. It is known from amplitude modulation identification experiments with cochlear implant recipients that update/stimulation rates of at least four times the modulation frequency are preferred for adequate analysis/coding of the signal (McKay, McDermott, & Clark, 1994).

The frequency channel envelope signals 212 generated by N-channel filter bank 204 are modified by a modulation depth enhancer (MDE) 214, as described herein, prior to further processing by speech processing unit 126 in accordance with the implemented speech coding strategy. Modulation depth enhancer 214 independently operates on the narrow-band envelope signals in each filter bank channel.

Modulation depth enhancer 214 comprises an envelope signal modifier 216 that modifies the envelope signals of selected frequency channels to increase the modulation depth of the envelope signal. Modulation depth enhancer 214 makes such modifications based on modification parameters 220 generated by modulation depth analyzer 218.

A maxima selection module 226 is configured to select a subset of the channels on which modified envelope signals 222 having the largest amplitude at a given instance in time. An encoder 224 is configured to use the selected channels to generate electrical stimuli corresponding in stimulus intensity and electrode number to the amplitude and frequency of the selected channels. External transmitter unit 128 provides this information to internal components 144 via an RF link.

Figure 3:
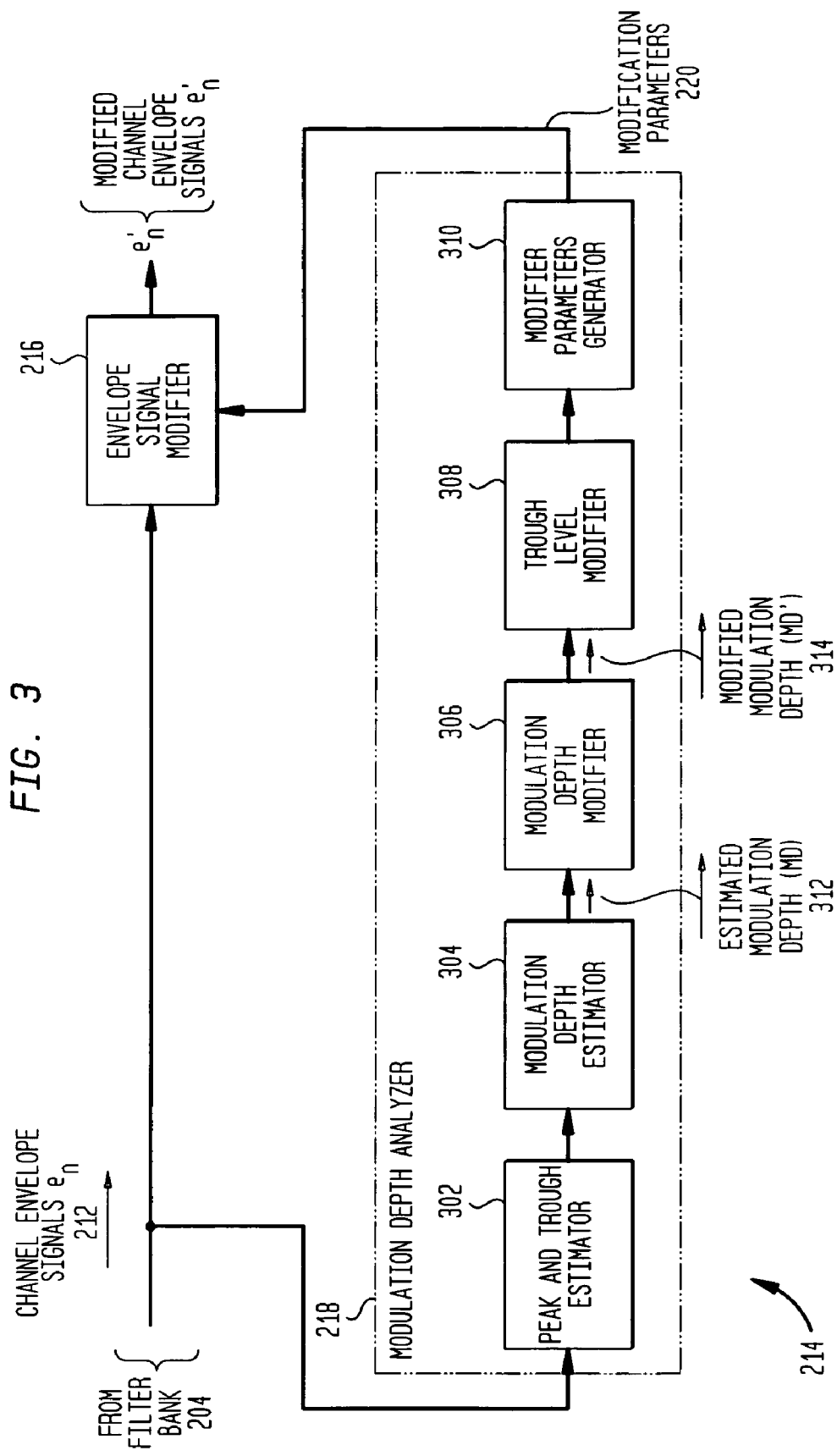
FIG. 3 is a functional block diagram of the modifier rules illustrated in FIG. 2, in accordance with one embodiment of the present invention.

FIG. 3 is a functional block diagram of one embodiment of the modulation depth analyzer 218 illustrated in FIG. 2. As noted in connection with FIG. 2, modulation depth anaylzer 218 receive frequency channel signals 212 from filter bank 204.

A peak and trough estimator 302 of modulation depth analyser 218 utilizes conventional techniques now or later developed to identify the maximum amplitude or peak ($P_n$) and the minimum amplitude or trough ($T_n$) of the envelope signal for each frequency channel. In one embodiment, the peak and trough levels of the envelope signal in each channel are estimated over a finite time period using a sliding time window of duration ($\tau$).

A modulation depth estimator 304 of modulation depth analyser 218 estimates the modulation depth of the envelope signals in each channel 212 based on the peak and trough values generated by estimator 302. In one embodiment, modulation depth estimator 304 applies the algorithm shown in Equation (1) to generate a corresponding estimated modulation depth 312.

$$MD_n = P_n/T_n \quad (1)$$

where,
n=channel number;
$P_n$=maximum envelope signal level in channel n over sliding time window of duration $\tau$; and
$T_n$=minimum envelope signal level in channel n over the same sliding time window of duration $\tau$.

The duration of the sliding time window ($\tau$) is typically 10 to 15 ms and is of sufficient duration to analyze fundamental voicing frequencies as low as 100 Hz.

For periodic voiced signals such as vowels, the maximum and minimum levels will respectively follow peak and trough envelope signal levels relatively accurately provided that: the voicing period is shorter than the duration ($\tau$) of the sliding time window; and that modulations in the signal at higher harmonic frequencies than the fundamental do not interfere with the modulation depth of the fundamental. For un-voiced signals, such as friction, which have no specific periodicity, the peak and trough levels (and thus the estimated modulation depth) can vary greatly from one peak-trough cycle to the next.

Because the modulation depth is estimated over some finite duration, rather than instantaneously, the estimate must be referenced from a time point corresponding to the middle of the time window. Thus a processing delay of $\tau/2$ is introduced for all processing following the modulation depth estimation performed by modulation depth estimator 304.

In one embodiment, the estimated modulation depth 312 for each channel is modified by modulation depth modifier 306 according to input/output functions to effectively increase the modulation depth. In this implementation, a power function is used to expand the modulation depth for cases when it is less than some knee point (typically 6 dB). The order of the power function is typically 2 or 3. For modulation depths greater than this knee point but less than some limit (for example, 20 dB), a linear function is used to modify the modulation depth. For modulation depths above this limit point the modulation depth is unchanged.

In one embodiment, modulation depth modifier 306 modifies the modulation depth in accordance with the following process:

For modulation depths less than or equal to a selected Knee point ($K_{MD}$), which typically equals 2 (6 dB), the modified modulation depth ($MD'_n$) 314 is increased using a power function where the Expansion Factor ($X_{MD}$), which is typically equal to 2 or 3, defines the order of the power function, as shown in Equation (2):

$$MD'_n = MD_n^{X_{MD}} \text{ for } MD_n \leq K_{MD} \quad (2)$$

For modulation depths greater than the Knee point but less than some Limit point ($L_{MD}$), which typically equals 10 (20 dB), the modulation depth is increased in accordance with a linear function, as shown in Equation (3).

$$MD'_n = MD_n \times A + B \text{ for } K_{MD} < MD_n < L_{MD} \text{ and } K_{MD}^{X_{MD}} < L_{MD} \quad (3)$$

where,
$A = (L_{MD} - K_{MD}^{X_{MD}})/(L_{MD} - K_{MD})$; and
$B = L_{MD} \times (1-A)$.

The constants A and B are calculated such that boundary conditions are satisfied (that is, no discontinuities) at the knee and limit points. That is, the constants A and B may be derived for the following boundary conditions: $MD'_n$ equals $MD_n^{X_{MD}}$ at the knee point (that is, when $MD_n = K_{MD}$) and $MD_n$ is unchanged (i.e. $MD'_n = MD_n$) at the Limit point. Note, $K_{MD}$ raised to the power of $X_{MD}$ must be less than $L_{MD}$.

For modulation depths above the Limit point, the modulation depth is left unchanged, as shown in Equation (4):

$$MD'_n = MD_n \text{ for } MD_n \geq L_{MD} \quad (4)$$

Figure 4:
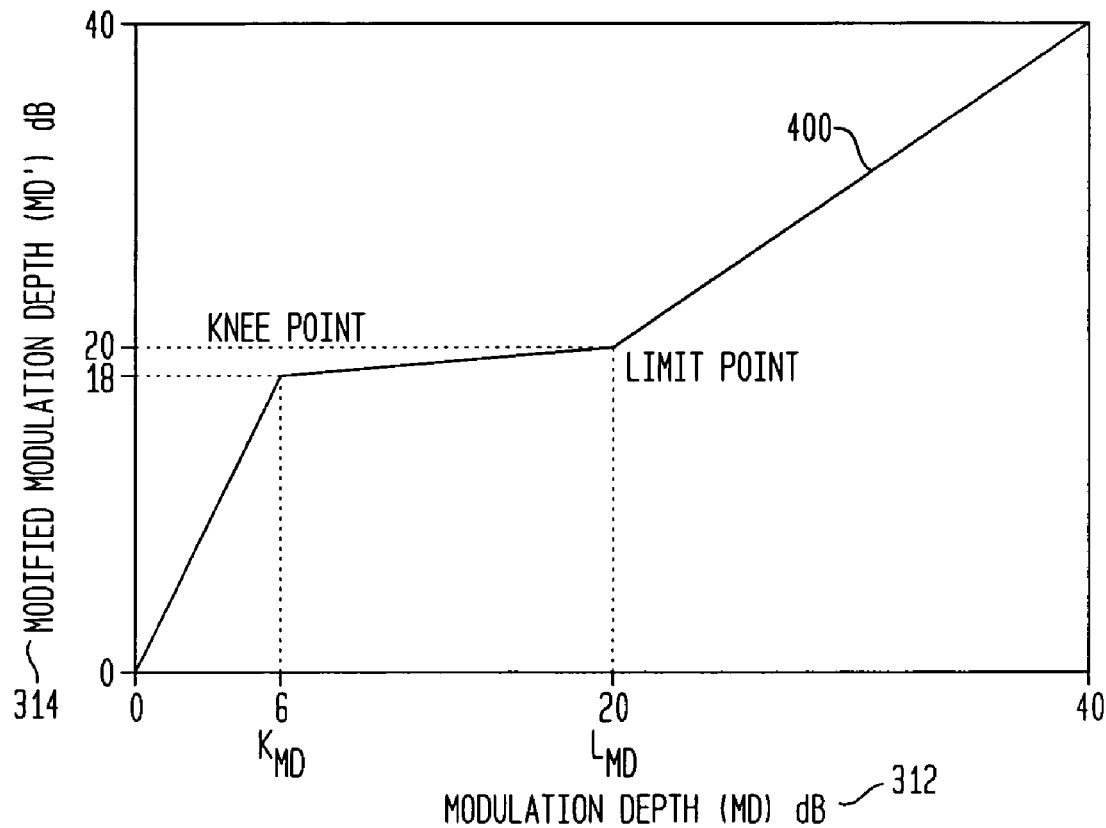
FIG. 4 is an example of an input/output function implemented in one embodiment of the present invention to modify the modulation depth of the envelope curve.

FIG. 4 is a curve illustrating one example of an input/output function implemented in modulation depth modifier 306. The curve 400 is plotted on a log-log dB scale, for the modulation depth using a Knee point of 2 (6 dB), a Limit point of 10 (20 dB), and an Expansion factor of 3.

The envelope signals ($e_n$) 212 are modified ($e'_n$) 222 so as to achieve the desired modifications to the modulation depth. Recall that the modulation depth is equal to the peak-to-trough ratio of $e_n$ calculated over some finite interval ($\tau$). Thus to increase the modulation depth either the peak level could be increased, the trough level could be decreased, or some function of both increasing the peak and decreasing the trough could be carried out. In order to minimize loudness changes when modifying the modulation depth, it might be desirable to keep the average level of the envelope signal constant. Thus both the peak and trough levels could be adjusted so as to preserve the average level. This approach would be recommended for non-cochlear implant prosthesis (such as hearing aids). However for cochlear implants, peaks of electrical stimulation contribute mostly to the perceived loudness of the signal and thus to minimize loudness changes, the peaks should be preserved and only the troughs of the envelope signals modified.

The modified modulation depth $MD'_n$ 314 is used by trough level modifier 308 to adjust the trough $T_n$ level of the envelope signal such that the modified trough level $T'_n$ is reduced by the ratio of the original modulation depth ($MD_n$) over the modified modulation depth ($MD'_n$). This is illustrated in Equation (5):

$$T'_n = T_n \times MD_n/MD'_n = P_n/MD'_n \qquad (5)$$

For cases when the envelope signal is at a trough (i.e. when $e_n = T_n$) the relationship shown in Equation (5) can be used to determine the modified trough level ($T'_n$) which is inversely proportional to the ratio of the modified modulation depth 314 over the original modulation depth 314. However for points in time where the envelope signal is not at a trough, the modified values for the envelope signal ($e'_n$) need to be calculated based on the required reduction to the trough level.

In one embodiment, a linear equation is implemented in envelope signal modifier 216 to modify the continuum of levels in envelope signals 212. Use of a linear function will preserve the shape of envelope signal 212 within each voicing period (or periodic cycle). One example of such a linear equation which may be employed to modify the continuum of levels in the envelope signal is shown in Equation (6).

$$e'_n = e_n \times C_n + D_n \qquad (6)$$

where,
$C_n = (P_n - T'_n)/(P_n - T_n)$; and
$D_n = P_n \times (1 - C_n)$.

Figure 5A:
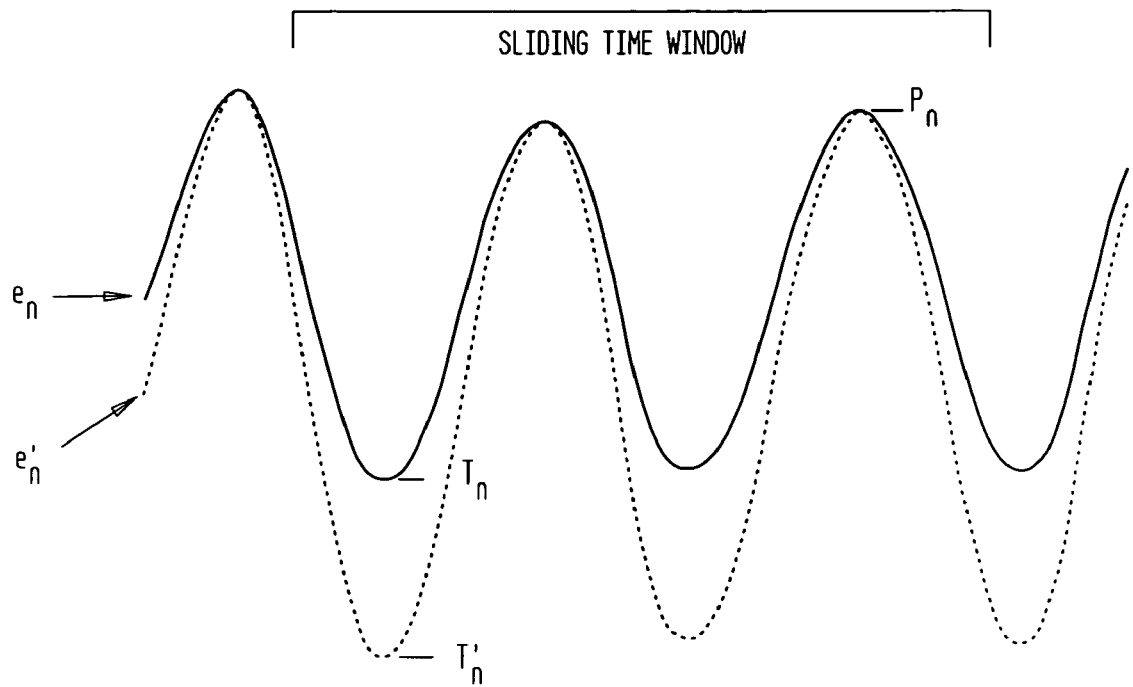
FIG. 5A depicts an exemplary envelope signal for a voiced passage of speech in a single channel and the subsequent modified envelope signal as processed by one embodiment of the modulation depth enhancer illustrated in FIG. 3.

Solutions for $C_n$ and $D_n$ determined by modifier parameters generator 310 (and thus $MD'_n$ determined by modulation depth modifier 306 and $T'_n$ determined by trough level modifier 308) are computed when either the peak or trough levels change. Constants $C_n$ and $D_n$ could be derived by parameter generator 310 such that the envelope signal is unchanged (that is, $e'_1 = e_n$) when the envelope signal is at a peak; and the envelope signal is adjusted according to the desired modulation depth increase (that is, $e'_n = e_n \times MD_n/MD'_n$) when the envelope signal is at a trough. Solution of $e'_n$ 222 generated by envelope signal modifier 216 is conducted for every time point in the envelope signal. FIG. 5A displays an exemplary unmodified envelope signal $e_n$ 212 and modified envelope signal $e'_n$ 222 in one channel for a typical voiced passage of speech.

It will be appreciated that the parameters used represent only one possible strategy possible under the implementation described. For example, the inventors have tested alternative parameters for the strategy. In one embodiment, a knee point of 10 dB, a limit point of 80 dB, and an expansion power of 7 (below the knee point) were implemented. This provides a greater expansion of modulation depth. An alternative embodiment provides more moderate expansion, with a knee point of 6 dB, a limit of 40 dB, and an expansion power of 4.

Alternate functions rather than a linear equation for modification of the continuum of levels in the envelope signal could be employed. For instance, it may be desirable to better preserve the peak level by using a second- or higher-order equation that adjusts levels in the trough region (that is, levels below the average or mid-point of the envelope signal) more than those in the peak region (that is, levels above the mid-point of the envelope signal). This would ensure less change to the loudness of the peaks and thus less change to the overall loudness of the perceived signal after processing. It will however distort the shape of the envelope signal within each voicing period.

Rather than using a second- or higher-order equation an alternate approach might use a linear equation but change the boundary conditions such that only trough regions (that is, levels below the mid-point of the envelope signal) are modified. The mid-point of the envelope signal could be defined as shown in Equation (7):

$$M_n = (P_n + T_n)/2 \qquad (7)$$

For cases when the envelope signal is above the mid-point no change to the signal would be applied. However for cases when the envelope signal is below the mid-point a linear equation could be employed to modify the signal such that mid-point levels are unchanged but levels at a trough are decreased by the desired increase to the modulation depth. The same linear equation as shown in Equation (6) could be used but the constants $C_n$ and $D_n$ would be adjusted by making reference to the mid-point $M_n$, as shown in Equation (8).

$$e'_n = e_n \times C_n + D_n \text{ for } e_n < M_n \qquad (8)$$

where,
$C_n = (M_n - T'_n)/(M_n - T_n)$; and
$D_n = M_n \times (1 - C_n)$

Figure 5B:
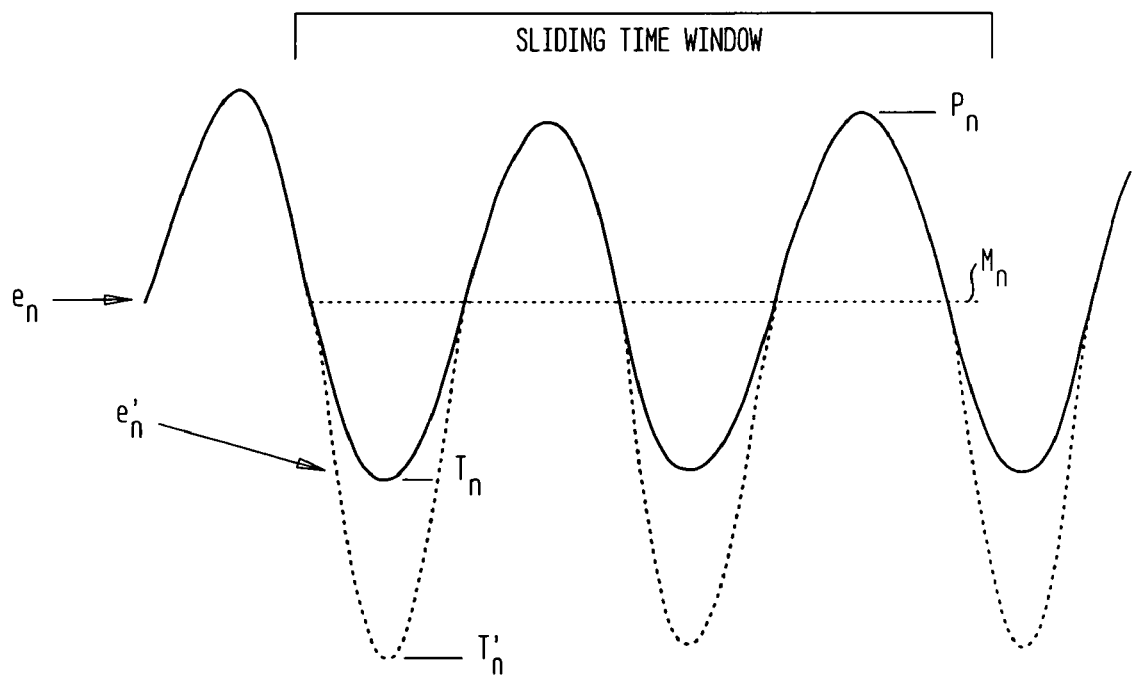
FIG. 5B depicts an exemplary envelope signal for a voiced passage of speech in a single channel and the subsequent modified envelope signal as processed by one embodiment of the modulation depth enhancer illustrated in FIG. 3.

Note, that this embodiment will preserve the shape of the envelope signal when it is above the mid-point and then stretch the signal when it is below the mid-point. FIG. 5B displays an example unmodified ($e_n$) and modified ($e'_n$) envelope signal that may be generated when this embodiment is implemented. Note also that in this embodiment, peak and trough estimator 302 will also calculate the mid-point level ($M_n$), and parameter generator 310 calculates $C_n$ and $D_n$ relative to the mid-point rather than the peak level.

The modified envelope signals $e'_n$ 222 replace the original envelope signals $e_n$ 212 derived from the filter bank 204 and processing then continues as per the original speech coding strategy. For the SMSP strategy (or the SPEAK and ACE strategies) M of the N channels of $e'_n$ having the largest amplitude at a given instance in time are selected at block 226 (typically M=8 for this embodiment). The M selected channels are then used by encoder 224 to generate M electrical stimuli corresponding in stimulus intensity and electrode number to the amplitude and frequency of the M selected channels.

These M stimuli are transmitted to internal components 144 of cochlear implant 100 via a radio-frequency link and are used to activate M corresponding electrode sites. The modulation depth enhancement may be applied to the channelized sound signal, and subsequent processing continues as per any selected processing strategy for cochlear implant 100. This strategy is specific to this stage of processing, and hence is applicable to any strategy which employs channelization and subsequent processing (with modifications as may be dictated by the requirements of the selected strategy).

Figure 7:
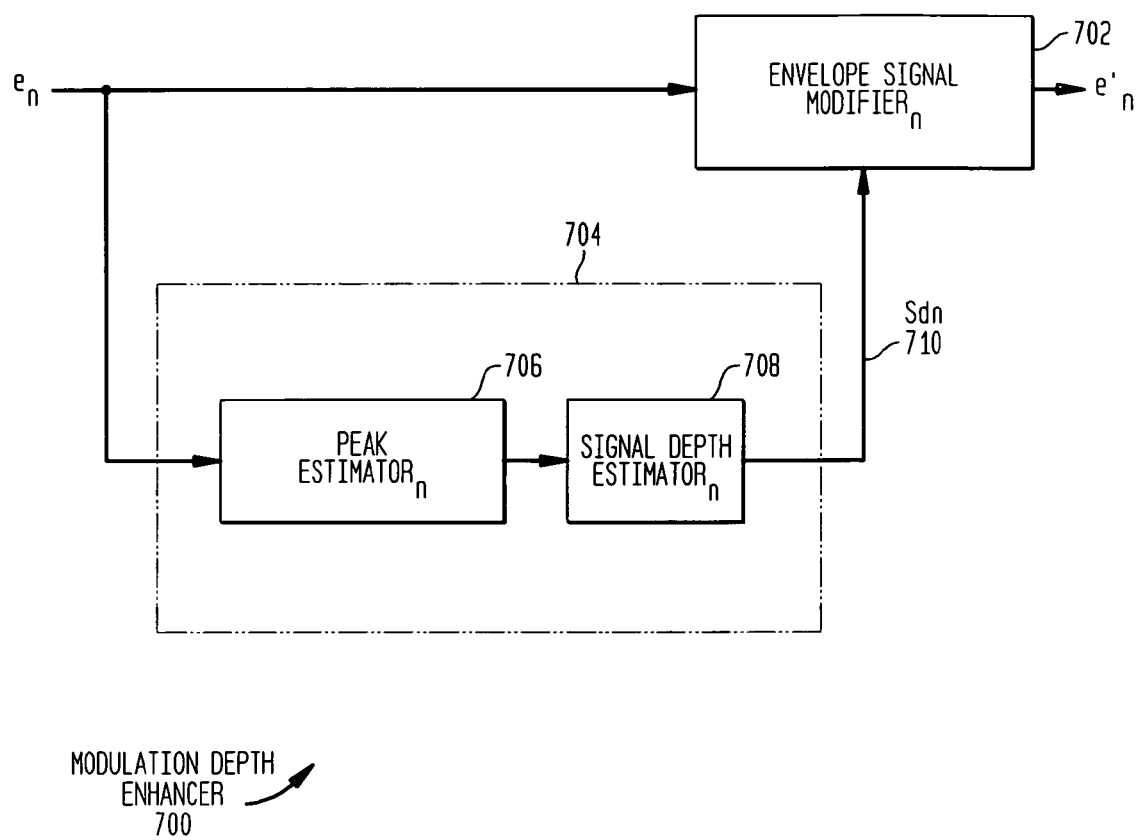
FIG. 7 is a schematic block diagram of an embodiment of the signal processing applied by an embodiment of the MDE algorithm.

It will be appreciated that many alternatives exist for expanding the modulation depth, and that the example in this implementation is only one alternative. An alternative approach for implementation of the algorithm that adjusts the envelope signal 212 based on the "signal depth" rather than the total modulation depth is illustrated in FIG. 7. This embodiment of modulation depth enhancer 214, referred to herein as modulation depth enhancer 700, comprises a modulation depth analyser 704 and an envelope signal modifier 702. Modulation depth analyzer 704 comprises a signal depth estimator 708 that generates a signal depth ($sd_n$) 710 that represents the ratio of the peak level (generated by peak detector 706) to the envelope signal level at any time point and be defined as shown in Equation (9). The "signal depth" will equal the true modulation depth when the signal is at a trough and will equal unity when the signal is at a peak. For all levels between the peak and trough the "signal depth" will be inversely proportional to the signal level.

$$sd_n = P_n/e_n \qquad (9)$$

The "signal depth" is calculated continuously and used to adjust the envelope signal level for all time points. Applying similar rules to those used above for modification of the modulation depth, and using the relation $e'_n = P_n/sd'_n$, equations for the modified envelope signal levels as a function of the "signal depth" can be implemented in envelope signal modifier 702. For example, envelope signal modifier 702 implements Equation (10) for "signal depths" less than or equal to the Knee point:

$$e'_n = P_n/sd_n^{X_{MD}} \text{ for } sd_n \leq K_{MD} \qquad (10)$$

And, for "signal depths" greater than the Knee point but less than the Limit point, envelope signal modifier 702 implements Equation (11)

$$e'_n = P_n/(sd_n \times A + B) \text{ for } K_{MD} < sd_n < L_{MD} \text{ and}$$
$$K_{MD}^{X_{MD}} < L_{MD} \qquad (11)$$

where,
$A = (L_{MD} - K_{MD}^{X_{MD}})/(L_{MD} - K_{MD})$; and
$B = L_{MD} \times (1-A)$.

For "signal depths above the Limit point the envelope signal level is preserved, as shown in Equation (12).

$$e'_n = e_n \text{ for } sd_n \geq L_{MD} \qquad (12)$$

Figure 8:
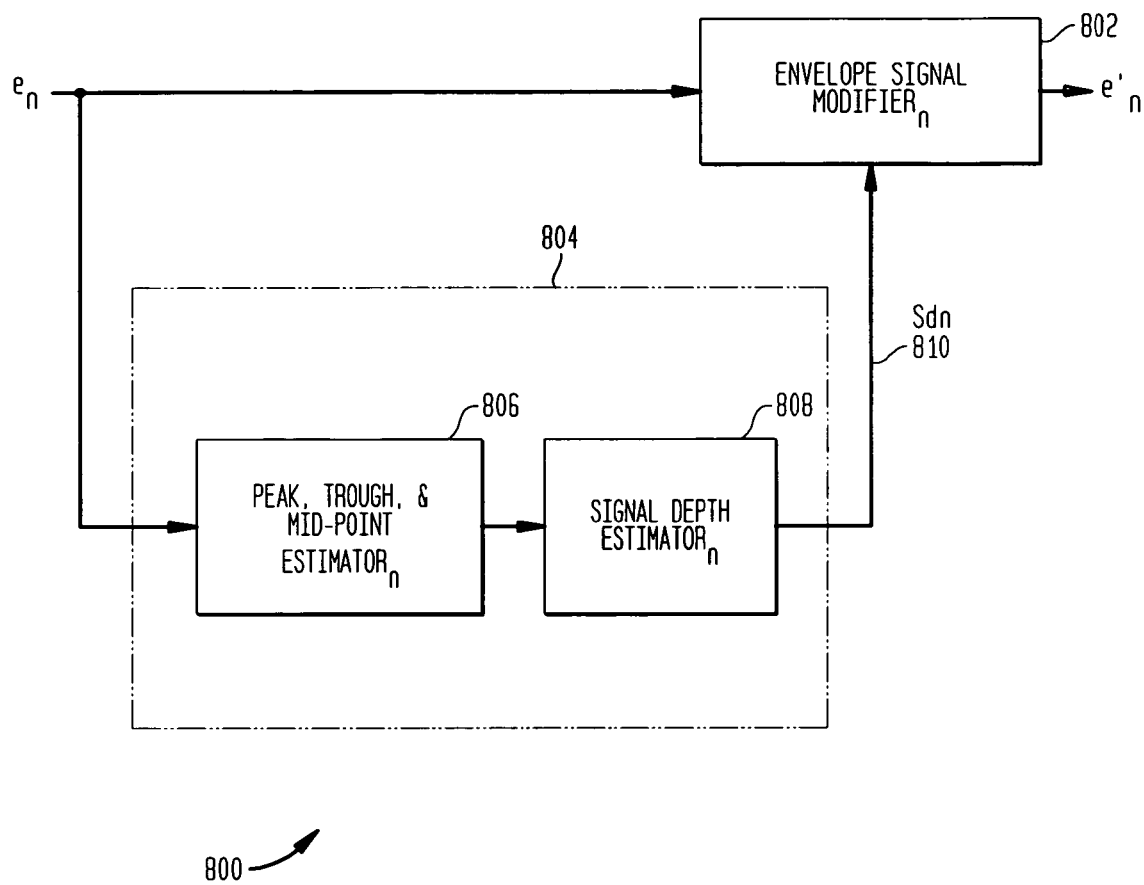
FIG. 8 is a schematic block diagram of an embodiment of the signal processing applied by an embodiment of the MDE algorithm.

FIG. 8 is a functional block diagram of another embodiment of modulation depth enhancer 214, referred to herein as modulation depth enhancer 800. Modulation depth enhancer 800 comprises an envelope signal modifier 802 and a modulation depth analyser 804. Modulation depth analyser 804 comprises a peak, trough and mid-point estimator 806 and signal depth estimator 808 operationally coupled as shown.

As in the embodiment described above in which only the trough region of the envelope signal is modified, the loudness of the processed signal might be better preserved by restricting envelope signal modifier 802 to perform signal modification to those time points in which envelope signal 212 is less than the mid-point (that is, $M_n$ as defined in Equation (7)) between its peak and trough levels. It is noted that computational time may be reduced as calculation of the "signal depth" is expensive as it requires a divide operation.

Modification of the envelope signal could simply be restricted to points in which the envelope signal is less than the mid-point (that is, $e_n < M_n$). As noted above, this will introduce distortion of the envelope signal (that is, a step change in the envelope signal level) at values around the mid-point. However, for cochlear implants this may not be problematic as it is unlikely that this sort of distortion is noticeable or destructive to the signal. For non-cochlear implant prostheses such as hearing aids this sort of distortion may be noticeable and should be avoided. In fact even the embodiment described above in which the envelope signal 212 is modified based on the signal depth can introduce inter-period distortion that may be noticeable and thus the linear approach described above with reference to Equations (1) through (6) is recommended for non-cochlear implant prostheses.

The distortion discussed above may be alleviated somewhat by re-defining the equation for the "signal depth", as shown in Equation (9), as a function of the mid-point, rather than the peak, of the envelope signal level.

$$sd_n = M_n/e_n \text{ for } e_n < M_n \qquad (13)$$

However the "signal depth" $sd_n$ now no longer equals the modulation depth when the signal is at a trough. Modifying Equation (13) so that the boundary conditions of:
$sd_n = 1$ at the mid-point (that is, for $e_n = M_n$); and
$sd_n = MD_n$ at a trough (that is, for $e_n = T_n$)
are met we obtain Equation (14):

$$sd_n = (2 \times M_n - e_n)/e_n \text{ for } e_n < M_n \qquad (14)$$

Referring to FIG. 8, similar modulation depth rules as used above in Equations (10), (11) and (12) can be used by envelope signal modifier 802 to derive equations for the modified envelope signal ($e'_n$) 214 as a function of the "signal depth" 810 generated by signal depth estimator 808 as defined in Equation (14) for all time point in $e_n$ which are less than the mid-point $M_n$ as determined at block 806. This embodiment is reflected in Equations (15), (16) and (17), respectively.

For "signal depths" less than or equal to the Knee point:

$$e'_n = M_n/sd_n^{(X_{MD}-1)} \text{ for } sd_n \leq K_{MD} \text{ and } e_n < M_n \qquad (15)$$

While for "signal depths" greater than the Knee Point but less than the Limit point:

$$e'_n = M_n/(sd_n \times A + B) \text{ for } K_{MD} < sd_n < L_{MD} \text{ and}$$
$$K_{MD}^{X_{MD}} < L_{MD} \text{ and } e_n < M_n \qquad (16)$$

where,
$A = (L_{MD} - K_{MD}^{X_{MD}})/(2 \times (L_{MD} - K_{MD}))$; and
$B = L_{MD} \times A + (1 - L_{MD})/2$.

For "signal depths: above the Limit point the envelope signal level is preserved.

$$e'_n = e_n \text{ for } sd_n \geq L_{MD} \qquad (17)$$

Note however that the rules differ slightly from those in Equations (10) . . . (12) because the "signal depth" is now relative to the mid-point, rather than the peak. In addition, for cases in which the modulation depth (or "signal depth") is small (that is, less than the knee point), the modulation depth expansion factor will be less than $X_{MD}$ (that is, approximately $X_{MD} - 0.5$).

Figure 6A:
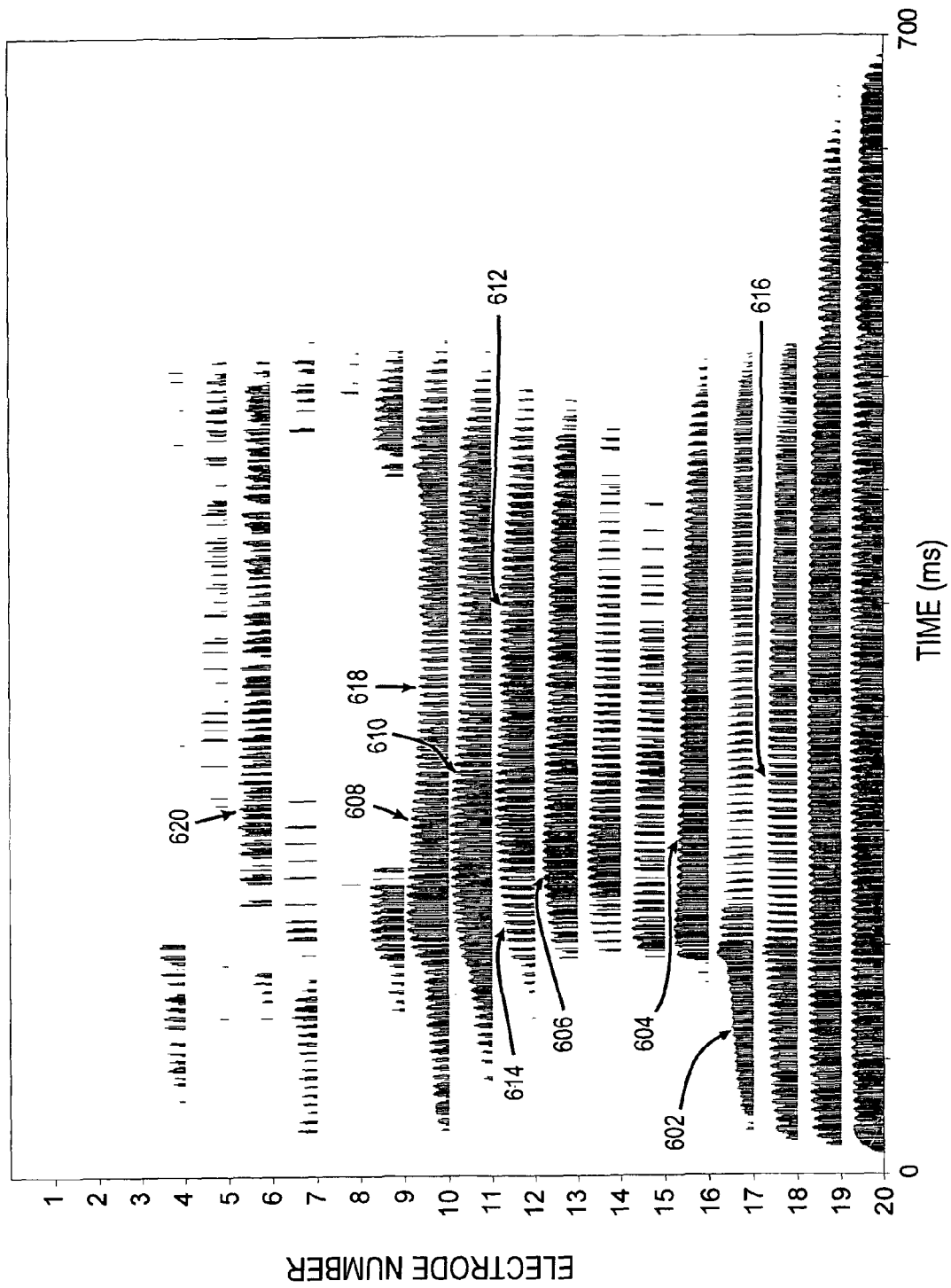
FIG. 6A is an electrodogram of sound signals to show the effect of implementing an embodiment of the present invention.
Figure 6B:
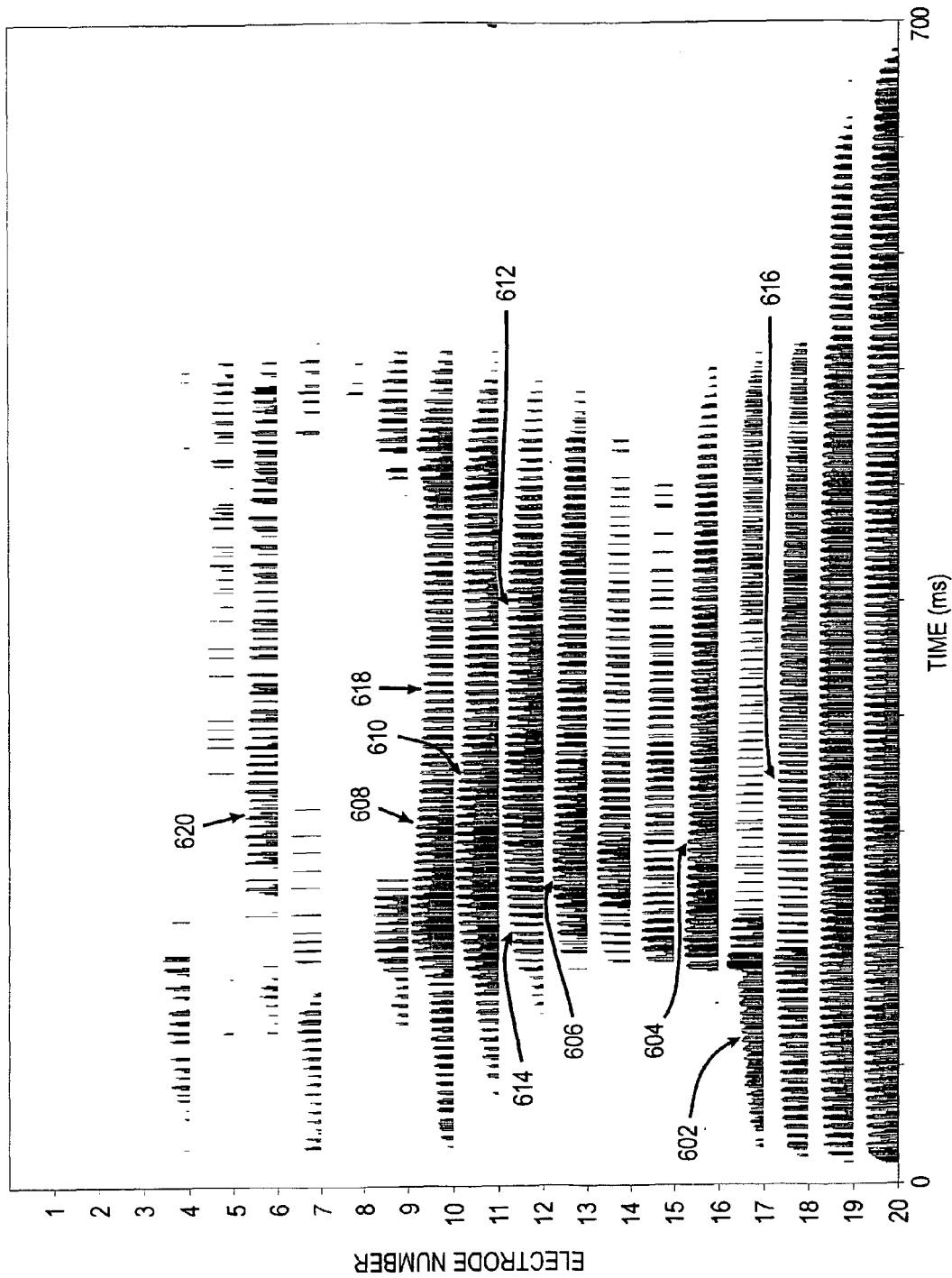
FIG. 6B is an electrodogram of sound signals to show the effect of implementing an alternative embodiment of the present invention.

To illustrate the effect of the strategy on the coding of speech signals, stimulus output patterns, known as electrodograms (which are similar to spectrograms for acoustic signals), which plot stimulus intensity (plotted as log current level) for each electrode (channel) as a function of time, were recorded for the SMSP and MDE strategies and are shown in FIGS. 6A and 6B, respectively. The speech token presented in these recordings was "lime" and was spoken by a female speaker having a fundamental voicing frequency of approximately 200 Hz. Note, the electrodogram for the MDE strategy depicts the response for the algorithm as described above with reference to Equations (13) through (17). The MDE Knee point was set to 6 dB, the Limit point to 20 dB and the Expansion factor to 3. The effect of the MDE strategy can be seen by comparing FIGS. 6A and 6B.

For cases where the unmodified modulation depth is small or less than the Knee point (for example, points 602, 604 and 606), the modified modulation depth is expanded by a factor of approximately 3 on a log scale. For cases where the unmodified modulation depth is above the knee point but below the Limit point (for example, points 608, 610 and 612)

the modulation depth is still expanded but by a factor less than 3 which approaches 1 as the modulation depth approaches the Limit point. For cases where the unmodified modulation depth is above the Limit point (for example, points 614, 616 and 618), the modulation depth is unmodified. Note, for unvoiced or noisy segments of the signal (for example, point 620) the modulation depth is still modified.

In certain embodiments of the present invention, the above MDE algorithm is configured or adapted to a form suitable for implementation in a real-time digital signal processor (DSP). At least two criteria may be considered in such embodiments. First, fixed-point DSP processing utilizes numerical values less than or equal to 1.0. Thus when parameters in the algorithm such the modulation depth (that is, the ratio of the peak-to-trough level which is a value that is always greater than or equal 1.0) the parameters must either be scaled such that they fall into a usable range below 1.0, or inverted (that is, reciprocal) such that they will never be greater than 1.0. For the case of the modulation depth (and "signal depth") inverted values are utilized. Second, DSPs are typically efficient at performing add, subtract and multiply operations, but not divisions. Thus the processing is preferably arranged so as to minimize the number of required division operations.

Conversion of the MDE algorithm described above with reference to Equations (1) through (8) is described next below. The modulation depth as per Equation (1) is inverted so as to never exceed 1.0.

$$MD_n = e_n/P_n \tag{1-DSP}$$

The Knee point and Limit point are subsequently inverted and Equations (2), (3) and (4) can be re-written as set out next below.

For inverted "signal depths" greater than or equal to the inverted Knee point, Equation (2) above can be re-written as set out in Equation (2-DSP):

$$MD'_n = MD_n^{XMD} \text{ for } MD_n \leq K_{MD} \tag{2-DSP}$$

For inverted "signal depths" less than the inverted Knee point but greater than the inverted Limit point, Equation (3) above can be re-written as set out in Equation (3-DSP):

$$MD'_n = MD_n \times A + B \text{ for } K_{MD} < MD_n < L_{MD} \text{ and } K_{MD}^{XMD} < L_{MD} \tag{3-DSP}$$

where,
$A = (L_{MD} - K_{MD}^{XMD})/(L_{MD} - K_{MD})$; and
$B = L_{MD} \times (1 - A)$ For inverted "signal depths" less than the inverted Limit point the envelope signal level is preserved, Equation (4) above can be re-written as set out in Equation (4-DSP):

$$MD'_n = MD_n \text{ for } MD_n \geq L_{MD} \tag{4-DSP}$$

The modified trough level (Equation (5)) can be expressed as a function of the modified inverted modulation depth ($MD'_n$), as set out in Equation (5-DSP):

$$T'_n = P_n \times MD'_n \tag{5-DSP}$$

In the embodiment described above in which linear Equation (6) is implemented to modify the envelope signal, the constant $C_n$ will always be greater than or equal to 1.0. Inverting $C_n$ will require a divide operation for each calculation of $e'_n$, thus it would be more efficient to scale $C_n$ (and thus $D_n$) by a factor of 1/S (where $S = 2^{12}$ for a 24-bit DSP) when storing these constants and inverse scaling of S can be applied to Equation (6) as shown in Equation (6-DSP). It is efficient to scale by a power of 2 because this can typically be performed using a barrel right or left shift operation in a DSP rather than a divide or multiply operation respectively.

$$e'_n = (e_n \times C'_n + D'_n) \times S \tag{6-DSP}$$

where,
$C'_n = (1/S) \times (P_n - T'_n)/(P_n - T_n)$; and
$D'_n = P_n \times (1/S - C'_n)$ Similarly, for the embodiment described above in which the envelope signal is modified in accordance with Equations (7) and (8), the mid-point of the envelope signal could be defined as shown in Equation (7), repeated here as Equation (7-DSP):

$$M_n = (P_n + T_n)/2 \tag{7-DSP}$$

When the envelope signal is below the mid-point, the inverse of linear Equation (8) above is as set out in Equation (8-DSP):

$$e'_n = (e_n \times C_n + D_n) \times S \text{ for } e_n < M_n \tag{8-DSP}$$

where,
$C'_n = (1/S) \times (M_n - T'_n)/(M_n - T_n)$; and
$D'_n = M_n \times (1/S - C'_n)$.

Conversion of the MDE algorithm described above with reference to Equations (9) through (12) for implementation in a DSP is described next below. The "signal depth" as per Equation (9) is inverted so as to never exceed 1.0, as shown in Equation (9-DSP):

$$sd_n = e_n/P_n \tag{9-DSP}$$

The Knee point and Limit point are subsequently inverted and Equations (10) through (12) may be re-written as set out next below.

For inverted "signal depths" greater than or equal to the inverted Knee point, Equation (10) may be inverted as shown in Equation (10-DSP):

$$e'_n = P_n \times sd_n^{XMD} \text{ for } sd_n \geq K_{MD} \tag{10-DSP}$$

For inverted "signal depths" less than the inverted Knee point but greater than the inverted Limit point, Equation (11) may be re-written as shown in Equation (11-DSP):

$$e'_n = P_n \times (sd_n \times A + B) \text{ for } K_{MD} > sd_n > L_{MD} \text{ and } K_{MD}^{XMD} > L_{MD} \tag{11-DSP}$$

where,
$A = (L_{MD} - K_{MD}^{XMD})/(L_{MD} - K_{MD})$, and
$B = L_{MD} \times (1 - A)$.

For inverted "signal depths" less than the inverted Limit point the envelope signal level is preserved, as shown in Equation (12-DSP):

$$e'_n = e_n \text{ for } sd_n \leq L_{MD} \tag{12-DSP}$$

Equations (14) through (17) can be employed with the restriction that the "signal depth" and thus the modified envelope signal level is only calculated when the envelope signal level is less than the mid-point level.

Alternatively, distortion may be alleviated by re-defining the "signal depth" as per Eq. (A2.6). Again the "signal depth" must be inverted so as to never exceed 1.0.

$$sd_n = e_n/(2 \times M_n - e_n) \text{ for } e_n < M_n \tag{14-DSP}$$

The Knee point and Limit point are subsequently inverted and Equations (15) through (17) can be re-written as set out next below.

For inverted "signal depths" greater than or equal to the inverted Knee point:

$$e'_n = M_n \times sd_n^{(XMD-1)} \text{ for } sd_n \geq K_{MD} \& e_n < M_n \tag{15-DSP}$$

For inverted "signal depths" less than the inverted Knee point but greater than the inverted Limit point, Equation (16) may be re-written as shown in Equation (16-DSP):

$$e'_n = M_n \times (sd_n \times A + B) \text{ for } K_{MD} < sd_n < L_{MD} \text{ and } K_{MD}^{XMD} < L_{MD} \text{ and } e_n < M_n \tag{16-DSP}$$

where, $A = 2 \times (L_{MD} - K_{MD}^{X_{MD}}) / [(L_{MD} - K_{MD}) \times (1 + L_{MD}) \times (1 + K_{MD}^{X_{MD}})]$; and $B = L_{MD} \times (2/(1 + L_{MD}) - A)$.

For inverted "signal depths" less than the inverted Limit point the envelope signal level is preserved, as shown in Equation (17-DSP):

$$e'_n = e_n \text{ for } sd_n \leq L_{MD} \tag{17-DSP}$$

D. Envelope Signal Phase Alignment

As noted, the amplitude-modulated narrow-band envelope signals 212 may differ in phase between frequency channels. The inventors have observed that phase differences between modulation signals in neighboring channels compromises recipients' ability to identify the modulation frequency, and that temporal pitch perception is improved when the temporal peaks across channels are aligned. The effect of phase alignment among the envelope signals of neighboring or adjacent frequency channels may be due to, for example, the temporal integration of signals across channels and/or the spread of the electrical stimulus current field.

Embodiments of this next aspect of the present invention, described next below, implement what is generally and collectively referred to herein as the phase alignment techniques to minimize the phase differences between peaks (that is, time difference between temporal peaks) in amplitude-modulated envelope signals across channels. Briefly, the envelope for each channel is determined and the temporal peaks are identified. In one embodiment, a timing offset is then applied to selected channel signals to reduce the phase differences between the temporal peaks. These phase-adjusted signals are then used as the basis for further processing. Some embodiments reduce the phase differences between channel signals across all channels using a common reference signal, reduce the phase differences between some channels and not others (for example aligning only channels within a certain frequency range), and align channels within different frequency bands to different reference signals.

In one specific embodiment, the present invention provides a sound processing process comprising: determining an envelope for each channel signal, the envelope being determined so as to retain information about the fundamental frequency; determining temporal peaks in the envelope of at least selected channel signals, the peaks being related to the fundamental frequency; and selectively applying a timing offset to adjust the timing of the peaks in the selected channel signals, the adjustment being made in response to a predetermined instruction set, so that the phase differences between the peak values in at least the selected channel signals are reduced.

In another specific embodiment, the present invention provides a sound processing process, comprising: determining for each channel signal a channel envelope that retains information about the fundamental frequency of the sound signal; determining a reference signal corresponding to the sum of channel envelopes in a plurality of channels; determining the timing of temporal peaks in each of the channel envelopes and in the reference signal, the peaks being related to the fundamental frequency of the sound signal; determining a timing offset for at least some of the channels, using a predetermined instruction set, by reference to at least the difference in timing between the peaks in the reference signal and the corresponding peaks in each channel envelope; adjusting the timing of the channel signal in the selected channel signals in accordance with the timing offsets, so that the phase differences between the peak values in at least the selected channel signals are reduced; and determining subsequent reference signals from a sum of the time-shifted signals in the channels.

According to one embodiment, to minimize the phase difference between channels a reference envelope signal is established to which the phase of the envelope signals in each channel can be aligned. Ideally, the modulation frequency of the reference signal corresponds to the fundamental voicing frequency of the input sound signal and is sufficiently robust to be resistant to the effects of competing noise. Next, a phase offset (or time shift) for each channel is determined so as to best align the peaks in the temporal envelope of each channel with that of the reference signal. In one embodiment, the time shift can be, for example, up to half the lowest expected voicing/modulation period (for 80 Hz this is approximately 6 ms) and can be a positive or negative time shift (i.e. ±6 ms). A temporal peak detection algorithm is preferably used to determine the location in time of maximum turning points (peaks) in the envelope signal. Small peaks or peaks too close in time are ignored. Having established the peak times for a channel, the peak times are aligned (if possible) with those of the reference signal by introducing a time shift to the channel in question.

In an alternative embodiment an optimum time shift is determined based on an analysis of the combination (product or summation or similar rule) of the reference signal and the frequency channel in question for all possible time shifts. Finally, the phase offset (time shift) is applied to each channel so as to minimize distortion of the envelope signals resulting from the time shift.

The reference signal in a preferred form is generated using an iterative procedure. Initially, all filter bank envelope signals are summed together over some finite time window. Given a positive signal-to-noise ratio at least some of the channels contain periodicity information pertaining to the fundamental voicing/modulation frequency. This reference signal is used to adjust the phase offset (time shift), using the techniques described herein, of each channel in turn for the given time window. Processing would then begin again for the next time window/pass except in this case the reference signal would be constructed by summing the time shifted channel signals together. Distortion in each channel due to dynamic adjustment of the time shift may be minimized by low-pass filtering the time shift and/or only applying it at time points for a given channel where its envelope signal is at a local minimum (temporal trough).

Provided that the fundamental voicing (or modulation) frequency of a substantial portion of the received sound signal is steady, the phase offset (time shift) for each channel will converge within a few iterations (time steps) on some value that aligns the temporal peaks of each channel. Furthermore, provided that the fundamental voicing or modulation frequency does not change too rapidly the phase alignment approach of the present invention will adapt and follow the changes in frequency over time. For unvoiced (non-periodic) signals the phase offset for each channel would vary randomly. However given that the location in time of temporal peaks for unvoiced signals varies randomly, this is unlikely to impose any adverse effects. For voiced (periodic) signals combined with noise, the present invention will align any periodic temporal patterns available in the envelope signals of each channel, with alignment errors being inversely proportional to some function of the signal-to-noise ratio.

The present invention may be implemented using alternative methods for generating or applying the reference signal, provided that the broad functional intention of supplying additional information about the fundamental frequency (F0) and reducing phase differences between channels is met.

Referring to FIGS. 9-12B, embodiments of the invention are described with reference to use with the Advanced Combinational Encoder (ACE) strategy (Vandali, et. al., 2000). Note, however that it could equally be applied to other speech coding strategies such as the Continuous Interleaved Sampling (CIS) strategy (Wilson, et. al., 1991), or any other system in which input sound signals are channelized before further processing. Although the present invention is principally described with reference to a cochlear implant system, the invention is not limited to such an implementation.

Figure 9:
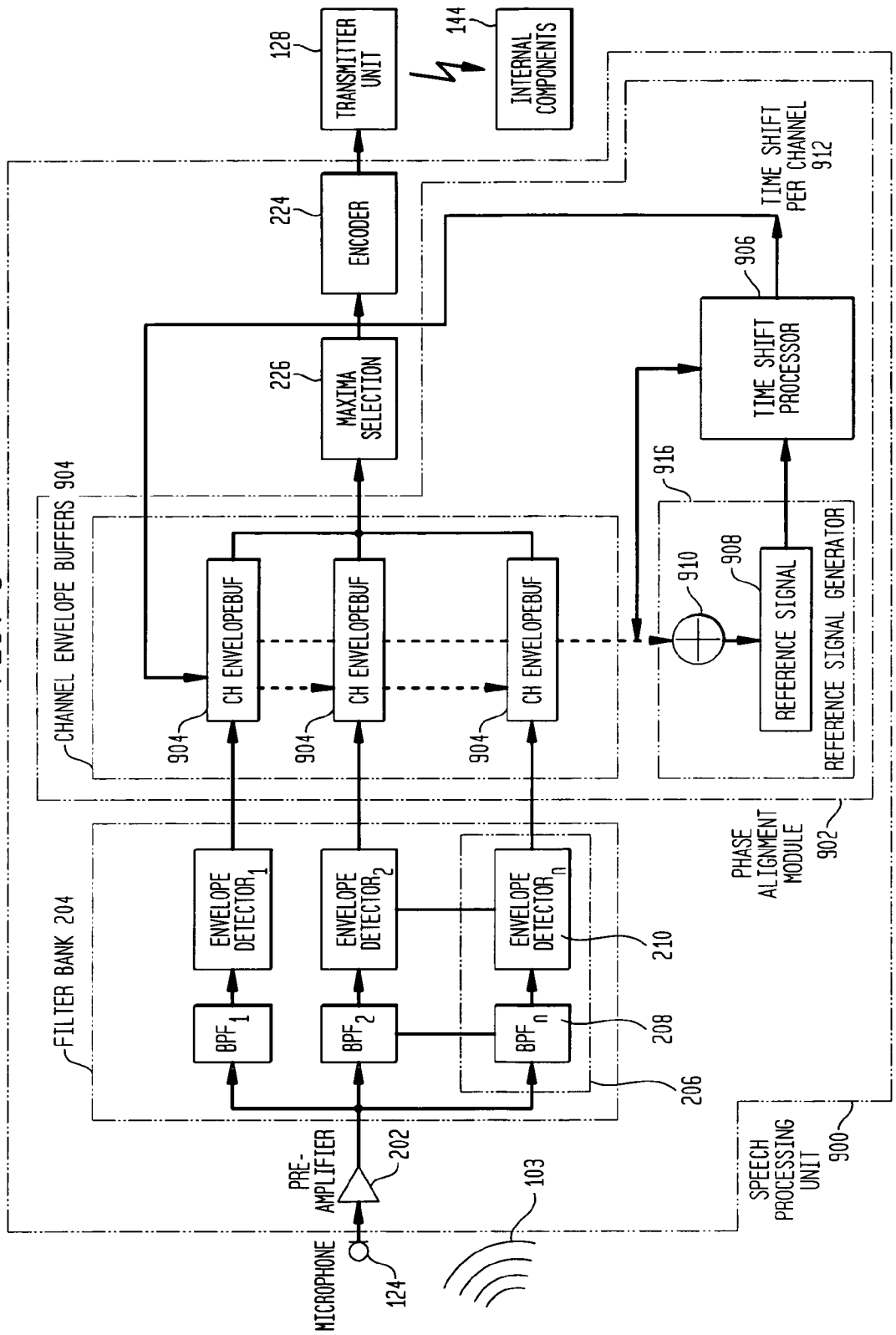
FIG. 9 is a schematic block diagram of one embodiment of the speech processing unit illustrated in FIG. 1.

Embodiments of the present invention are described herein in the context of a sound processing device that channels the input sound signal 103 into a plurality of spaced frequency channels. In the embodiments introduced above, speech processing unit 126 implements a filter bank 204 comprising band-pass filters 206 and envelope detectors 210 for estimating the narrow-band envelope signal (which include both the slow envelope components of less than 50 Hz and higher envelope frequencies up to approx 400 Hz) of the signal in each spaced frequency channel ("frequency channel signal" herein). FIG. 9 is a schematic block diagram of one embodiment of the speech processing unit illustrated in FIG. 1, referred to herein a speech processing unit 900.

As noted above, electrical signals corresponding to sound signals received via microphone 124 and pre-amplifier 202 are processed by a bank 204 of N parallel filters 208 tuned to adjacent frequencies (typically N=20 for the ACE strategy). Each filter channel 206 includes a band-pass filter 208 and an envelope detector 210 to provide an estimate of the narrow-band envelope signal 212 in each channel. Band-pass filters 208 may be narrow (approximately 180 Hz wide –3 dB bandwidth) for apical (low-frequency) channels and increase in bandwidth (typically up to 1000 Hz or more) for more basal (higher frequency) channels. Envelope detectors 210, which effectively comprise a full-wave (quadrature) rectifier followed by a low-pass filter, typically pass fundamental (modulation) frequency information up to approximately 200 Hz but for some implementations (including this preferred embodiment) can accommodate frequencies as high as approximately 400 Hz.

Filter bank 204 is used to provide an estimate of the envelope signals 212 in each channel at regular time intervals known as the analysis or update rate. The ACE strategy can employ an update rate which can be adjusted from as low as approximately 200 Hz up to as high as approximately 4000 Hz (depending on the hardware device used). In this aspect of the present invention, an update rate of approximately 1200 Hz (or 1600 Hz) is employed so that modulation frequencies of approximately 300 Hz (or 400 Hz) can be adequately sampled (note, amplitude modulation identification experiments with recipients of cochlear implant prostheses have indicated that update/stimulation rates of at least four times the modulation frequency are required for adequate analysis/coding of the signal, McKay, McDermott, & Clark, 1994).

It is desirable that for each intended application, the envelope is determined so as to retain information about the fundamental frequencies for the intended application. In the context of speech, the range covering the voicing frequency (F0) should be captured. Otherwise, the desired pitch information will not be supplied to the recipient.

The outputs 212 of N-channel filter bank 204 are then processed by the phase alignment module 902 which minimizes the phase difference (or align temporal peaks) between amplitude-modulated envelope signals 212 across channels n, prior to further processing by the speech coding strategy. In one embodiment, this is carried out for all channels in the system, while in an alternative embodiment, this is carried out for at least those channels in the voiced frequency range (i.e. first, second and third formant frequency range which ranges from approximately 100 Hz up to 3 to 4 KHz). Other channel selection criteria may be implemented in alternative embodiments.

Phase alignment module 902 comprises an array of channel envelope buffers 904, a reference signal generator 916 and a time shift processor 906. Phase alignment module 902 is illustrated in greater detail in FIGS. 10 and 11. The channel envelope signals 212 derived from filter bank 204 are stored in channel envelope buffers 904 which are used by reference signal generator 916 to construct a reference signal 908 and are further used by time shift processor 906 to calculate appropriate time shifts 912 for each channel so as to align temporal peaks in the reference signal to those of channel signals.

The calculated time shifts 912 are applied to envelope signals 212 of each channel. These time shifted envelope signals 914 effectively replace the original envelope signals 212 derived from filter bank 204 and processing then continues as per the original speech coding strategy. For the ACE strategy M of the N channels having the largest amplitude at a given instance in time are selected at block 226 (typically M=8 for this embodiment). The M selected channels are then used by encoder 224 to generate M electrical stimuli 8 corresponding in stimulus intensity and electrode number to the amplitude and frequency of the M selected channels. These M stimuli are transmitted to internal components 144 of cochlear implant 100 via a radio-frequency link and are used to activate M corresponding electrode sites. This algorithm may be applied to the channelized sound signal, and subsequent processing continues as per any chosen processing strategy for the cochlear implant. This strategy is specific to this stage of processing, and hence is applicable to any strategy, which employs channelization and subsequent processing (with modifications as may be dictated by the requirements of the selected strategy).

It will be understood that alternative techniques could be used to determine the time shifts, and to apply them to the channel signals, within the scope of the present invention.

The first task of phase alignment module 902 is to construct a reference signal 908 for which envelope channel signals can be aligned to. The duration of the reference signal should be sufficiently long to contain at least two cycles of the modulation signal (i.e., at least two temporal peaks). Setting a lower limit of approximately 80 Hz for fundamental voicing frequencies to be analysed by this system dictates a minimum duration of 2×1/80=25 milliseconds (ms) for the reference signal buffer 908 length. In this implementation, initially the time shifts (phase offsets) for all channels are initialized to zero and reference signal 908 is generated by summing 910 channel envelope signals 212 for each time point into the reference signal buffer. However, in subsequent time frames the time shifts will vary and thus will result in construction of the reference signal from time shifted channel envelope signals. The time shift can be up to half the lowest expected voicing/modulation period (for 80 Hz this is approximately 6 ms) and can be a positive or negative time shift (i.e. ±6 ms). Thus, the channel envelope signal buffers 904 which hold the channel envelope signals 212 used to construct the reference signal 908 must be at least the length of the reference signal buffer (25 ms) plus twice the maximum time shift (2×6 ms) which equals 37 ms.

When constructing reference signal 908 from channel envelope signals 212, any channels that contain modulated signals that are aligned in phase with respect to one another will sum constructively so as to enforce the modulated signal in reference signal 908. In contrast, channels that contain modulated signals 212 that are out of phase with one another will tend to diminish or introduce additional peaks in reference signal 908. Modulated signals that are 180 degrees out of phase will be the most destructive.

For voiced speech input signals it is anticipated that reference signal 908 (that is, combination of all channels) will contain modulation terms that are related to the fundamental frequency of the received sound signal 103 but that the strength of these terms will vary with characteristics of the input signal and the band-pass filter bank 204 used to analyse the input signal. It is also anticipated that higher frequency modulation terms may be present in reference signal 908. The relative amplitude of the fundamental frequency signal to the higher frequency modulation terms will also vary with characteristics of input signal 103 and band-pass filter-bank 204. However, in subsequent time frames, if the time shifts for each channel are adjusted so as to align temporal peaks then this will result in strengthening of the fundamental frequency terms in reference signal 908.

The next task of the phase alignment module 902 is to determine appropriate time shifts 912 for each channel. In FIG. 11, time shift processor 906 depicts the processing path for this operation for one channel envelope signal 212. FIG. 11 is a schematic block diagram of one embodiment of time shift processor 906.

A peak detector 1102 is used to determine the relative time-location of all temporal peaks in reference signal 908 by finding all maximum turning points in the signal. Setting an upper limit of approximately 330 Hz for the fundamental voicing frequencies to be analyzed by this system suggests that temporal peaks closer than 1/330=3 ms should be ignored, or rather the smaller of the two peaks should be discarded. If two or more temporal peaks in reference signal 908 (over a 25 ms period) are located (that is, a modulation frequency equal to or higher than 80 Hz is present) then calculation of the phase offset (or time shift) for the channel envelope signals 212 that best aligns their peaks in time to those of reference signal 908 are determined.

This is carried out for each channel by determining the time-location of all temporal peaks (excluding those closer than 3 ms apart) in the channel envelope signal, using peak detector 1104, and determining the time shift required for each temporal peak that will align it with the peaks located in reference signal 908. Specifically, for each of the peaks located by the channel peak detector 1104, the channel envelope signal 212 is shifted in time and stored in buffer 1106 so as to align the peak with a peak in reference signal 908. A correlation, of sorts, between reference signal 908 and the shifted channel envelope signal is then performed by multiplier 1108, adder 1110 and time shift determinator 1114.

The correlation is carried out by multiplying at multiplier 1108 each time point in the time-shifted channel envelope signal 1106 by each time point in the reference signal 908 and summing at adder 1112 the multiplied terms 1110. These operations are carried out consecutively for all peaks in the channel envelope signal 212 and reference signal 908. An optimal time shift is then determined at block 1114 by selecting the smallest time shift (from peak detector 1104), compared to the current time shift, which provides the largest correlation term (derived from adder 1112). These operations are carried out for all channels and the optimal time shifts are then used to shift the channel envelope signal buffers 904 in time. The time shifted channel envelope signals from block channel envelope buffers 904 are referenced from a time point mid-way through the channel envelope buffers plus or minus the time shift. Thus an average delay of half the channel envelope buffer length (37/2=18.5 ms) will be introduced by this algorithm.

Figure 12A:
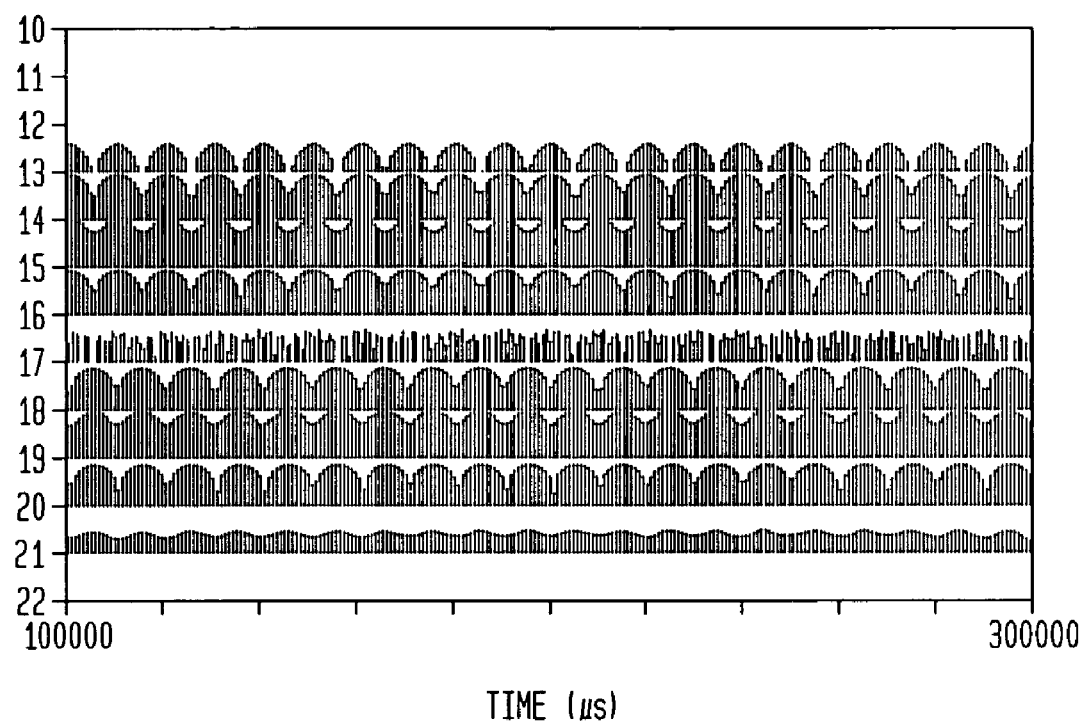
FIG. 12A is a display of a stimulus output pattern, or electrodogram, of amplitude modulated sound signals reflecting the effect of the implementation of one embodiment of the present invention.
Figure 12B:
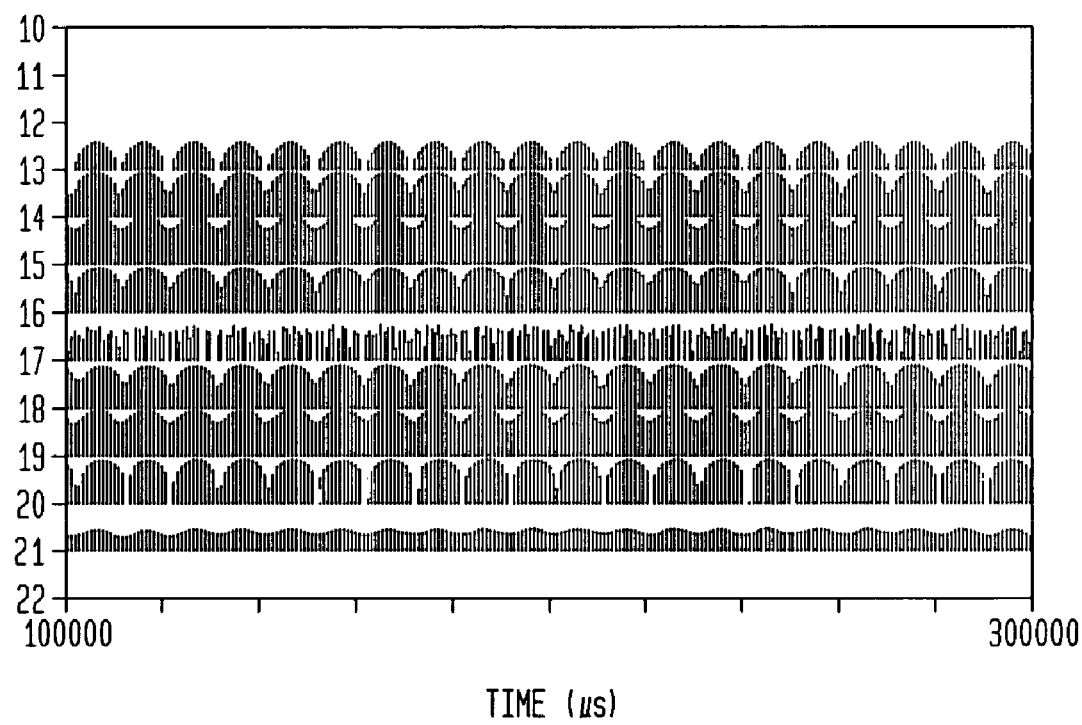
FIG. 12B is a display of a stimulus output pattern, or electrodogram, of amplitude modulated sound signals reflecting the effect of the implementation of one embodiment of the present invention.

To illustrate the effect of the phase alignment algorithm on the coding of amplitude modulated sound signals, stimulus output patterns, known as electrodograms (which are similar to spectrograms for acoustic signals), which plot stimulus intensity (plotted as log current level) for each electrode (channel) as a function of time, were recorded for the ACE strategy shown in FIG. 12($a$) and for application of the phase alignment to the ACE strategy shown in FIG. 12($b$). The sound signal used in these recordings include two sinusoidal amplitude modulated (SAM) pure tones of frequencies 600 and 1200 Hz respectively. The modulation frequencies for both SAM tones was 100 Hz and the modulation phase difference between SAM tones was 180 degrees.

For the standard ACE strategy in FIG. 12($a$), it can be seen that the envelope of the stimulus signals on electrodes 13 to 16 are 180 degree out-of-phase with those of electrodes 18 to 21. In contrast with application of the phase alignment algorithm to the ACE strategy in FIG. 12($b$), it can be seen that all electrodes carrying periodic modulation are now in phase. Note, the stimulus signal on electrode 17 is not very periodic and is not affected much by the algorithm.

In alternative embodiments, additional processing and/or optimizations may be carried out to improve the performance of phase alignment module 902. Such additional processing and/or optimizations may include one or more of the following.

In one embodiment, distortion in channel envelope signals 212 may be reduced by only applying an adjusted time shift value when the channel envelope signal level is at a trough (valley) or by low-pass filtering the time shift values.

In another embodiment, interactions between harmonic frequencies and the frequency boundaries imposed by filter bank 204 result in envelope channel signals 212 that contain periodic signals that follow the fundamental frequency but contain additional temporal peaks. These additional peaks lie between those of the underlying F0 pattern and introduce higher frequency modulation terms (for example, 2 or 3 times F0). In addition, the presence of noise will also introduce temporal peaks in the envelope signals, which are unrelated to the F0 periodicity.

One approach to reducing some of these effects is to smooth (low-pass filter) the reference signal using an integration window (finite impulse response filter) of length related to an estimate of the fundamental voicing frequency (F0). Alternatively, a fixed low-pass filter could be employed with a cut-off frequency of approximately 100 Hz that will attenuate the effect of higher order harmonics when F0 is low (that is, around 80-150 Hz).

In a further embodiment, some of the processing blocks are bypassed when the signal level is small (e.g. below some threshold in which the effect of the algorithm will go unnoticed).

In a still further embodiment, processing time is reduced by calculating reference signal 908 and tine shifts 912 at a lower frequency (for example, decimation of the time shift operations by a factor of 2 or 4).

It should be appreciated by those of ordinary skill in the art that the present invention can be applied to all or only some of the channel signals. For example, a reference signal may be generated based only upon a band of channels, and used only to modify the phase of those signals. An example of this may be to modify phase only for signals in a range corresponding to voiced signals, and not modify other channels. In this instance, appropriate buffer times will be required to compensate for processing delays in other channels.

Since modifications within the spirit and scope of the invention may be readily effected by persons skilled in the art, it is to be understood that the invention is not limited to the particular embodiment described above. In addition to the reference signal based approach, the invention encompasses alternative approaches to reduce phase differences between channels.

E. Multi-Channel Envelope Modulation (MEM) Strategy

This aspect of the present invention is generally directed to modulating the narrow band envelope signals in each channel by a broadband envelope signal derived from the input sound signal, such that the phase of modulated signals in the narrow band channels are synchronized. For voiced or periodic signals, the broadband envelope signal contains modulation components related to the fundamental frequency of the input sound signal. In the specific case of speech, this includes the voicing frequency. Consequently, modulation information related to the fundamental frequency is provided concurrently in time on all narrow band channels. Additionally, in certain embodiments, the modulation depth (for voicing frequency components, for example) in the broadband envelope signal is increased, and accordingly the average modulation depth in each narrow-band channel is generally increased, so that the modulation frequency information may be more reliably perceived by the recipient.

As with the above aspects of the present invention, this aspect of the invention includes a sound processing device adapted to channel input sound signal 103 into a plurality of spaced frequency channels, such as speech processing unit 126 introduced above.

Figure 13:
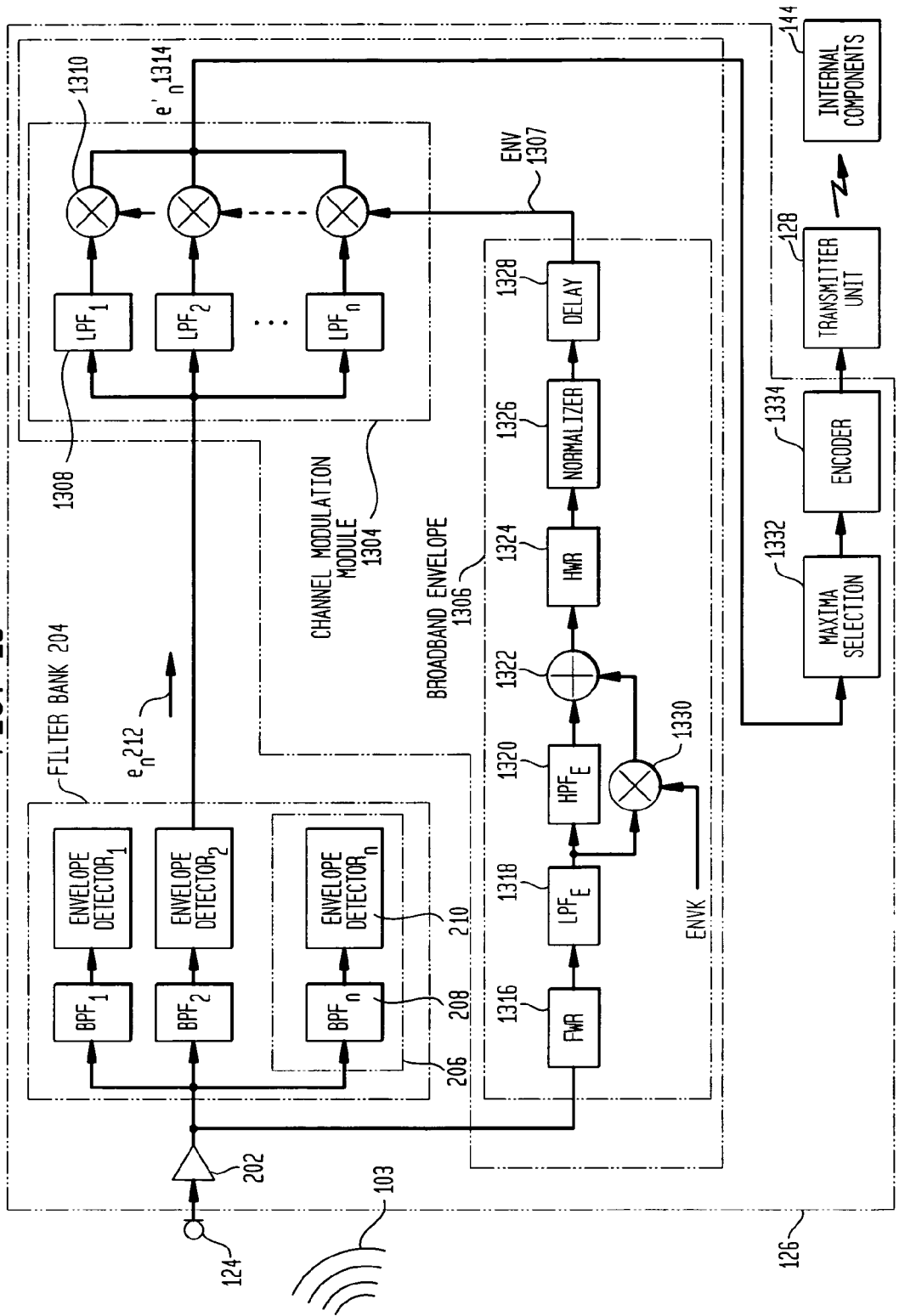
FIG. 13 is a schematic representation of the signal processing applied to the sound signal in accordance with the present invention.

In the embodiment illustrated in FIG. 13, the channelization of the input sound signal is attained by a filter bank 204 as described above. Filter bank 204 comprises band-pass filters 208 and envelope detectors 210 that estimate the narrow-band envelope signal (which include both the slow envelope components of less than 50 Hz and higher envelope signal frequencies up to approx 400 Hz) of the signal in each spaced frequency channel.

In the embodiment of the invention illustrated in FIG. 13, a broadband envelope detector 1306 measures the envelope of the broadband signal (for example, over a frequency range of 0 to 8 KHz) or a few broadband regions of the signal (for example, 0 to 4 KHz and 4 to 8 KHz); that enhances periodic information (for example, expanding the modulation depth of periodic terms) in the broadband envelope signal(s); and channel modulation module 1304 that uses the broadband envelope signal(s) 1307 to modulate the channelized narrow-band envelope signals 212 in unison.

This aspect of the invention, referred to herein as the Multi-channel Envelope Modulation (MEM) strategy, is described with reference to its use with the Advanced Combinational Encoder (ACE) strategy (Vandali, et al., 2000, Skinner, et al., 2002). The ACE strategy is similar to the Spectral Maxima Sound Processor (SMSP) strategy (McDermott, & Vandali, 1991; McDermott, McKay, & Vandali, 1992) and the Spectral Peak (SPEAK) strategy (Skinner, et al., 1994; Whitford, et al., 1995) but generally utilizes a higher electrical stimulation rate. The invention is also equally applicable to other coding strategies such as the Continuous Interleaved Sampling (CIS) strategy (Wilson, et al., 1991).

As with the ACE strategy, electrical signals corresponding to sound signals received via a microphone 124 and pre-amplifier 202 are processed by a bank 204 of N parallel filters 210 tuned to adjacent frequencies (N can be adjusted but typically=20). Each filter channel 206 includes a band-pass filter 208 and an envelope detector 210 to provide an estimate of the narrow-band envelope signal 212 in each channel $e_n$. Band-pass filters 208 are typically narrow (approximately 180 Hz wide −3 dB bandwidth) for apical (low-frequency) channels and increase in bandwidth (typically up to 1000 Hz or more) for more basal (higher frequency) channels. Envelope detectors 210, which effectively comprise a full-wave (quadrature) rectifier followed by a low-pass filter, typically pass fundamental (modulation) frequency information up to approximately 200 Hz but for some implementations can accommodate frequencies as high as approximately 400 Hz.

The filter bank is used to provide an estimate of the narrow-band envelope signals ($e_n$) in each channel at regular time intervals known as the analysis or update rate. The ACE strategy employs an update rate which can be adjusted from as low as approximately 200 Hz up to as high as approximately 4000 Hz (depending on the hardware device used). In the present invention an update rate of approximately 1200 Hz (or 1600 Hz) is employed so that modulation frequencies of approximately 300 Hz (or 400 Hz) can be adequately sampled (note, amplitude modulation identification experiments with users of cochlear implant prostheses have indicated that update/stimulation rates of at least four times the modulation frequency are required for adequate analysis/coding of the signal (McKay, McDermott, & Clark, 1994).

Figure 14:
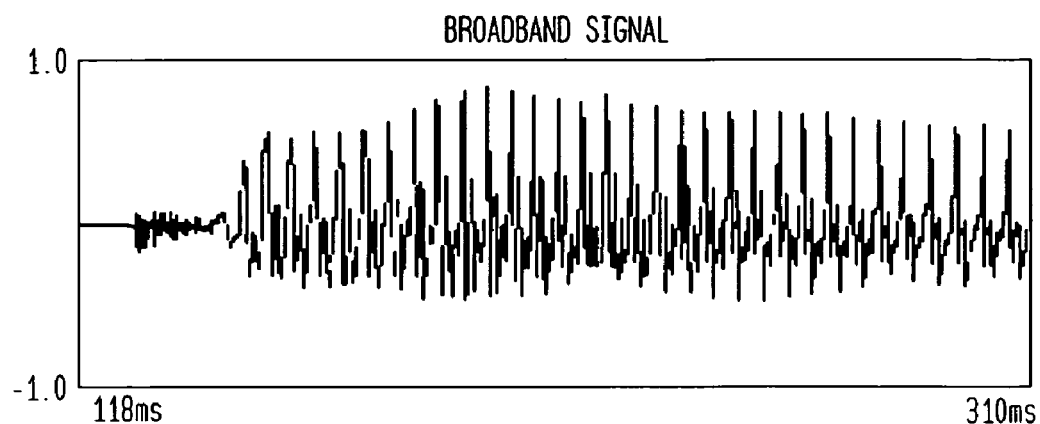
FIG. 14 depicts a signal waveform at various locations in the schematic representation of the signal processing path of one embodiment of the invention.
Figure 15:
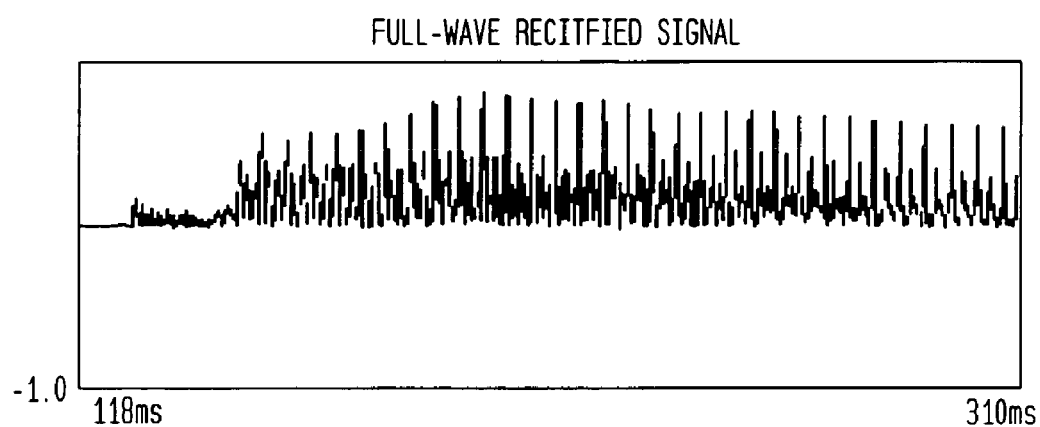
FIG. 15 depicts a signal waveform at various locations in the schematic representation of the signal processing path of one embodiment of the invention.
Figure 16:
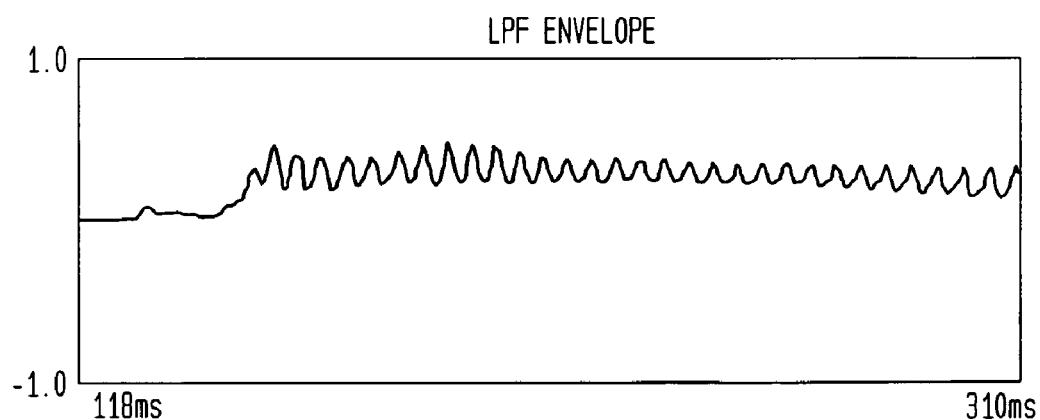
FIG. 16 depicts a signal waveform at various locations in the schematic representation of the signal processing path of one embodiment of the invention.

Processing for the MEM strategy then takes place in two separate paths as described in the following sections. FIGS. 14 through 22 will be used to illustrate the signal waveform at various locations in processing path. The signal used in these figures is the utterance "dog" spoken by a female speaker with an F0 of approximately 190 Hz. Note, only a portion of this utterance is depicted in these figures. First, the envelope of broadband signal 1307 as shown in FIG. 14 is derived by broadband envelope detector 1306. The output of preamplifier 202 is provided to a full-wave rectifier 1316 that full-wave rectifies the signal to generate the signal shown in FIG. 15. This signal is provided to a low-pass filter 1318 which, in one embodiment, applies a 300 Hz, $6^{th}$ order Butterworth, infinite impulse response (IIR) to generate the LPF envelope shown in FIG. 16.

Figure 17:
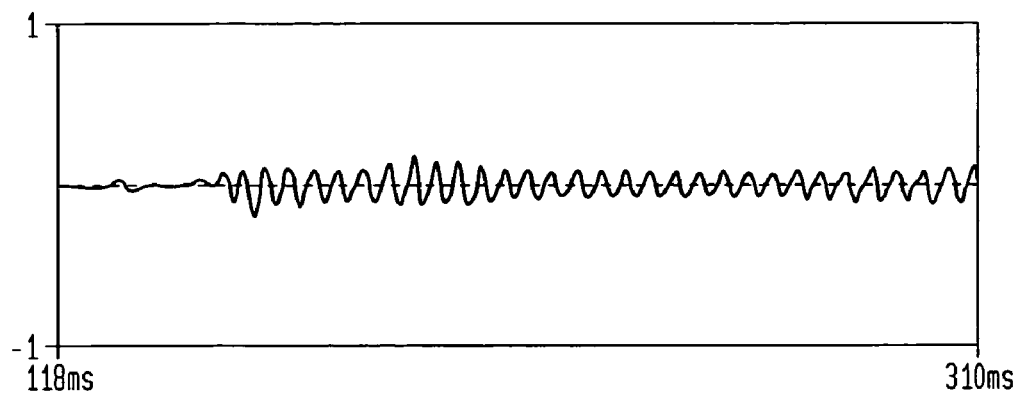
FIG. 17 depicts a signal waveform at various locations in the schematic representation of the signal processing path of one embodiment of the invention.
Figure 18:
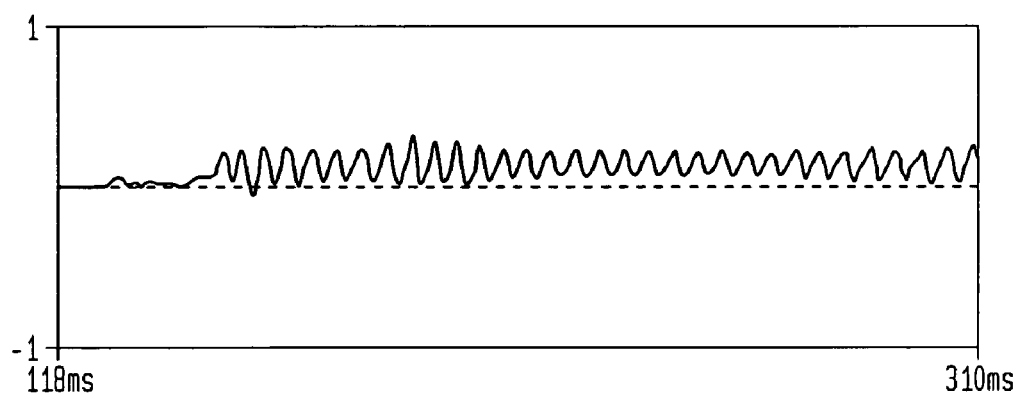
FIG. 18 depicts a signal waveform at various locations in the schematic representation of the signal processing path of one embodiment of the invention.

The broadband envelope signal is then provided to a high-pass filter 1320. High-pass filter 1320 removes the direct current (d.c.) and effectively expands modulation components corresponding to fundamental frequencies in the voiced speech range of 80 to 300 Hz. In one embodiment, high-pass filter 1320 is an 80 Hz, $2^{nd}$ order Butterworth, IIR high-pass filter. The resulting signal is shown in FIG. 17. A scaled version of the low-pass filtered signal generated by LPF 1318 is added to the envelope signal generated by high-pass filter 1320 by adder 1322. The resulting signal is illustrated in FIG. 18. As will be described in greater detail below, this allows for control of the expansion factor (or increase) applied to the modulation depth.

The broadband envelope signal is then provided to a half-wave rectifier 1324 that half-wave rectifies the signal to remove any negative excursions in the signal that may arise from the high-pass filtering process performed at block 1320. The scaling factor (EnvK) used to scale the low-pass filtered signal at multiplier 1330 can range from 0 to 8 and is typically equal to 0.5. Adjustment of the scaling factor (EnvK) allows for control of the expansion factor applied to the modulation depth in the envelope signal, with lower values providing deeper modulation. A scaling factor of 0.5 increases the modulation depth by a power of 3 approximately (at least for small modulation depths). For larger modulation depths, infinite expansion (or 100% modulation depth) is provided.

The expansion power for the modulation depth is given by the equation P≈(EnvK+1)/EnvK which holds for modulation depths in the original envelope of less than approximately 2×EnvK+1. Thus for EnvK=0.5, the expansion power is P≈3 for input modulation depths ≦2 (or 6 dB). For higher input modulation depths, P approaches infinity (or 100% modulation depth). FIG. 35 depicts the input/output function for modulation depth plotted on log dB scales for values of EnvK ranging from EnvK=infinity (P=1) down to EnvK=0.25 (P=5). Note, the slope of these functions are approximately equal to P for modulation depths approximately 2×EnvK+1.

Figure 19:
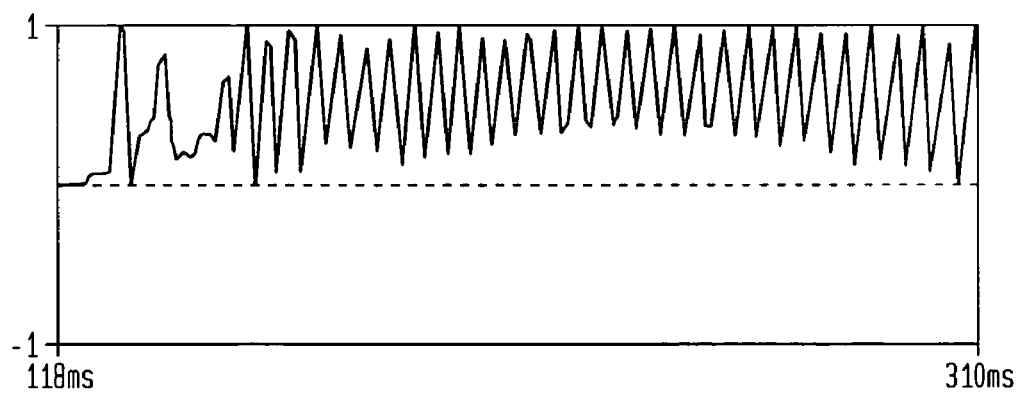
FIG. 19 depicts a signal waveform at various locations in the schematic representation of the signal processing path of one embodiment of the invention.

The expanded broadband envelope signal generated by half-wave rectifier 1324 is provided to normalizer 1326 which scales or normalises the amplitude of the signal such that its peak (or maximum) level over a finite time interval, which is measured using a sliding time window of approximately 12 ms in duration, is set to unity. This is achieved by multiplying the signal level by the inverse of the peak level derived from the sliding time window. Thus, the broad-band envelope signal is normalized to occupy a range of values from 0.0 to 1.0 with peak excursions (within a 12 ms interval) always reaching unity. The resulting signal is illustrated in FIG. 19.

Figure 20:
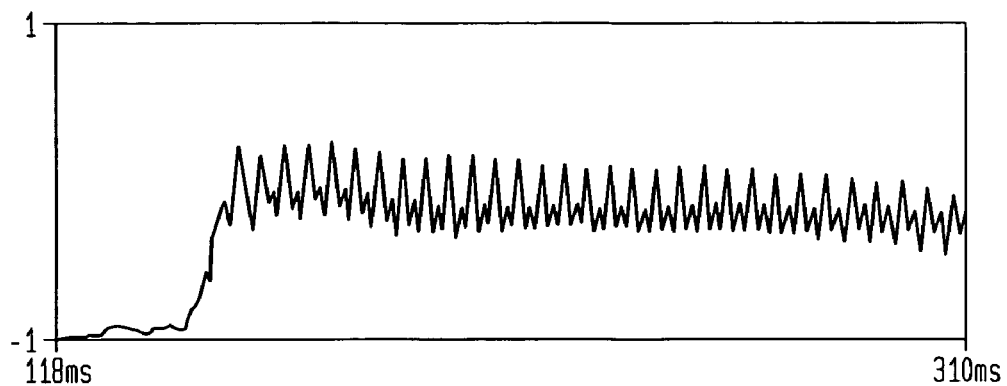
FIG. 20 depicts a signal waveform at various locations in the schematic representation of the signal processing path of one embodiment of the invention.
Figure 21:
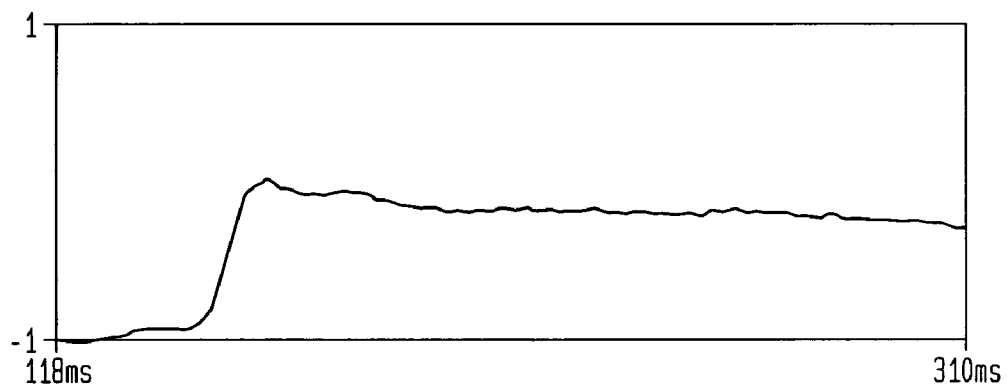
FIG. 21 depicts a signal waveform at various locations in the schematic representation of the signal processing path of one embodiment of the invention.
Figure 22:
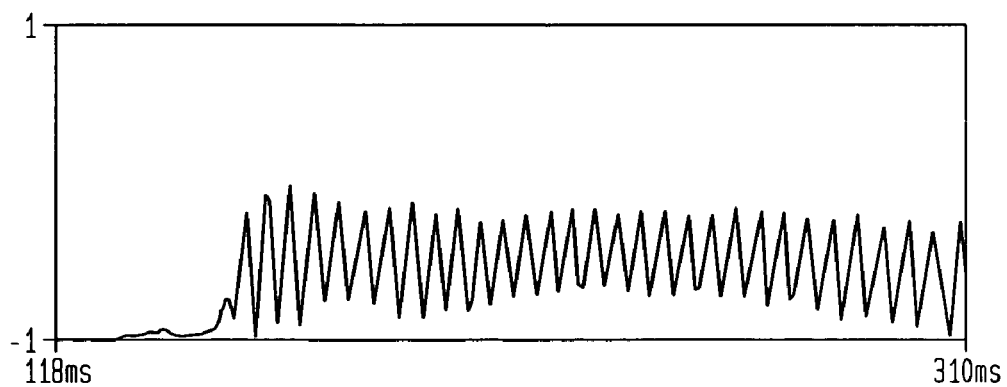
FIG. 22 depicts a signal waveform at various locations in the schematic representation of the signal processing path of one embodiment of the invention.

The normalized broadband envelope signal 1307 is then used by channel modulation module 1304 to modulate the narrow-band envelope signals 212 derived from the N-channel filter bank 204 of the ACE strategy. FIG. 20 depicts a narrow-band envelope signal 212 derived from the frequency range of approximately 100 to 300 Hz. The narrow-band envelope signals 212 are first low-pass filtered at block 1308 to generate the signal shown in FIG. 21. In one embodiment, low-pass filter 1308 is a 50 Hz, $2^{nd}$ order Butterworth, IIR LPF. This removes any amplitude modulation in envelope signals 212 corresponding to typical fundamental frequencies in voiced speech signals. It will be understood that at this stage, the narrow band envelope signals 212 contain little more than level information. These smoothed (low-pass filtered) envelope signals generated by low-pass filter 1308 are then modulated at multipliers 1310 by normalized broadband envelope signal 1307 illustrated in FIG. 22. Due to differences in the propagation time (or delay) through the broadband envelope signal path and the band-pass filter bank path, the broadband envelope signal is delayed at block 1328 by approximately 6 ms prior to being used to modulate the narrow-band envelope signals.

The N-channel modulated narrow-band envelope signals ($e'_n$) 1314 are then processed as per the normal ACE strategy. A subset (M) of the channels having the largest amplitude at a given instance in time are selected by maxima selector 1332 for further processing (typically M=10 for this embodiment). The M selected channels are then used to generate M electrical stimuli by encoder 1334 corresponding in stimulus intensity and electrode number to the amplitude and frequency of the M selected channels. These M stimuli are transmitted to implanted components 144 via a radio-frequency link established between transmitter unit 128 and a receiver included in internal components 144, and are used to activate M corresponding electrode sites.

Figure 23:
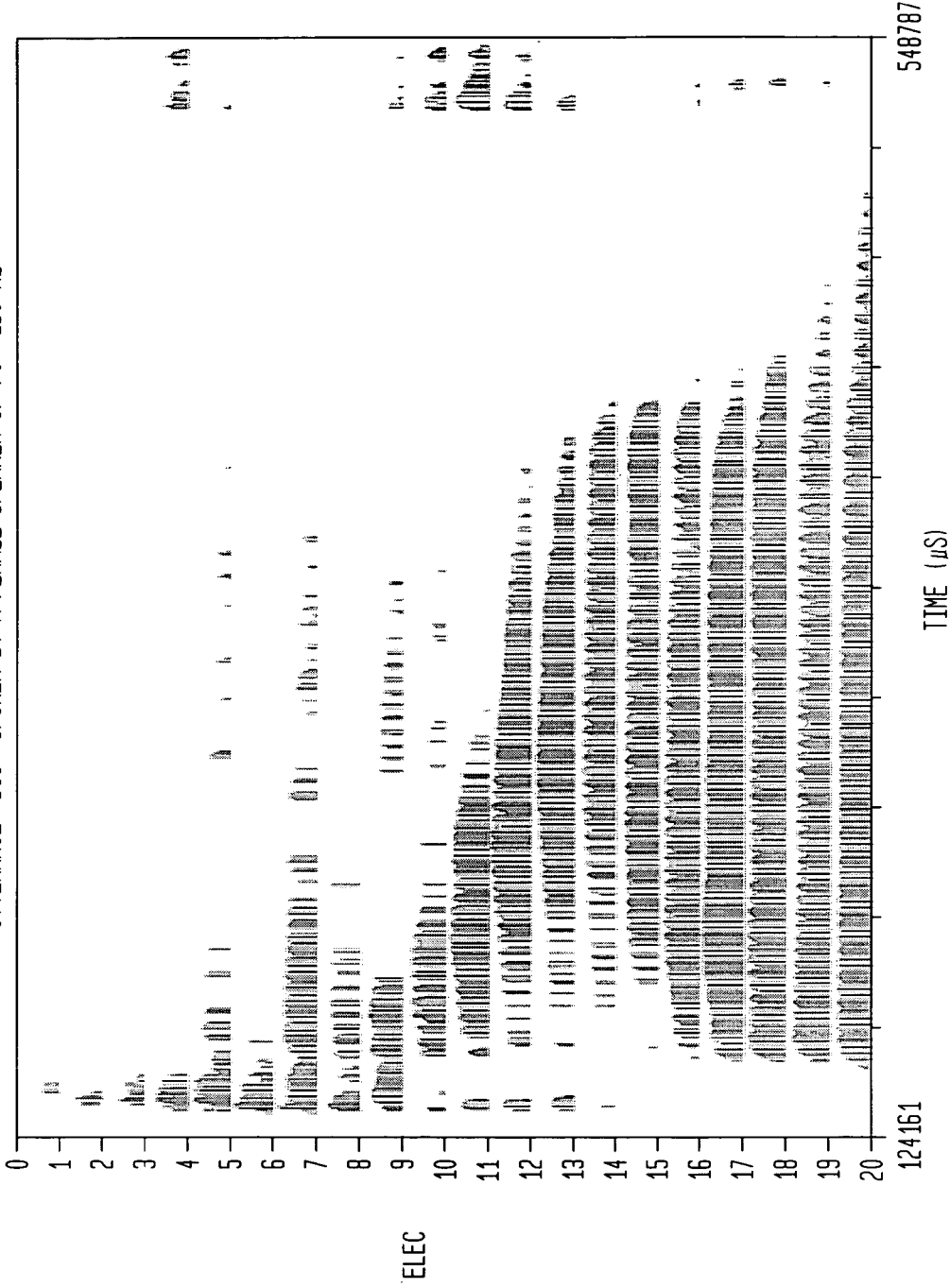
FIG. 23 is an electrodogram (stimulus output pattern) of sound signals to show the overall effect of the implementation of one embodiment of the present invention.
Figure 24:
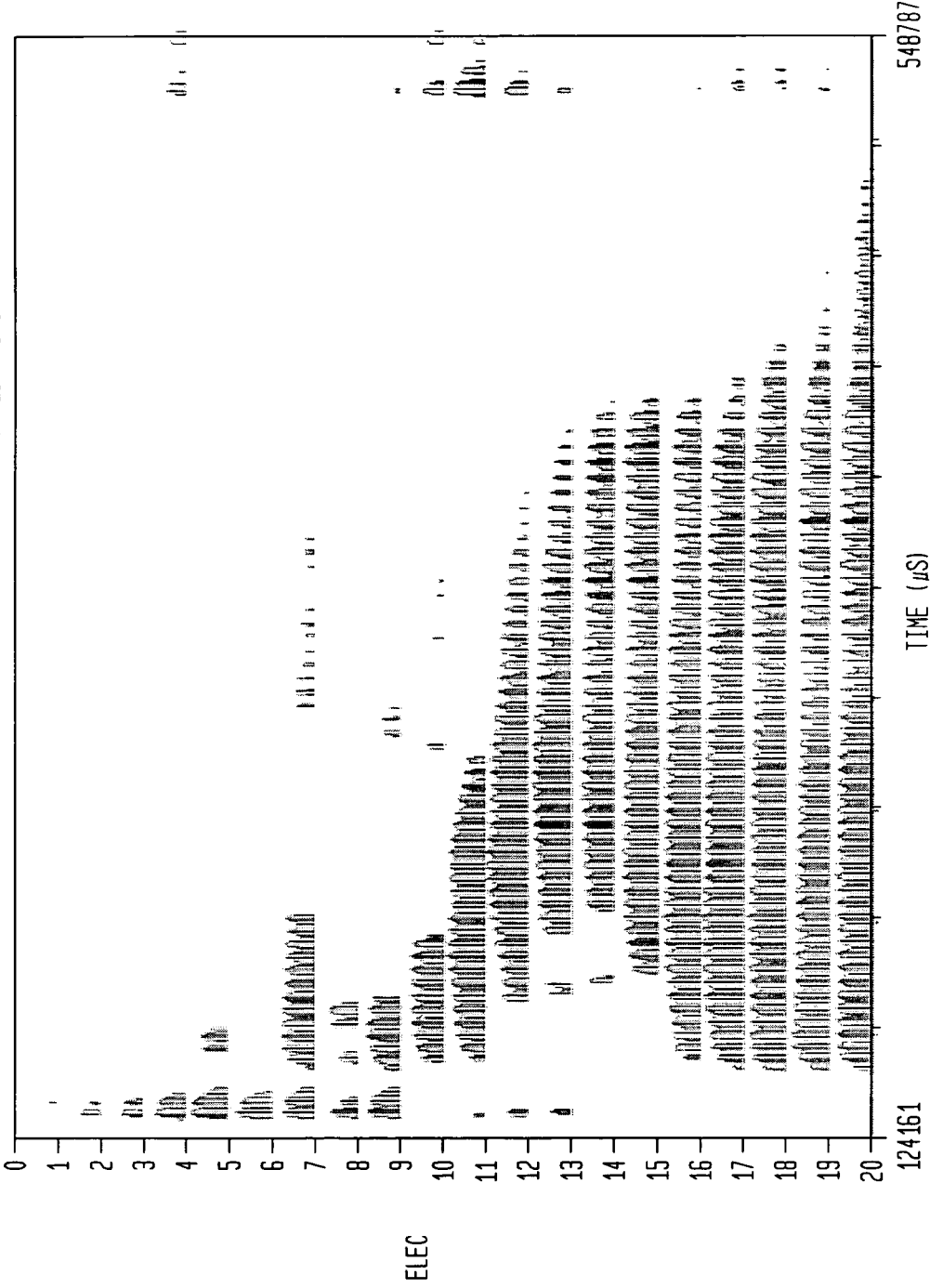
FIG. 24 is an electrodogram (stimulus output pattern) of sound signals to show the overall effect of the implementation of one embodiment of the present invention.
Figure 25:
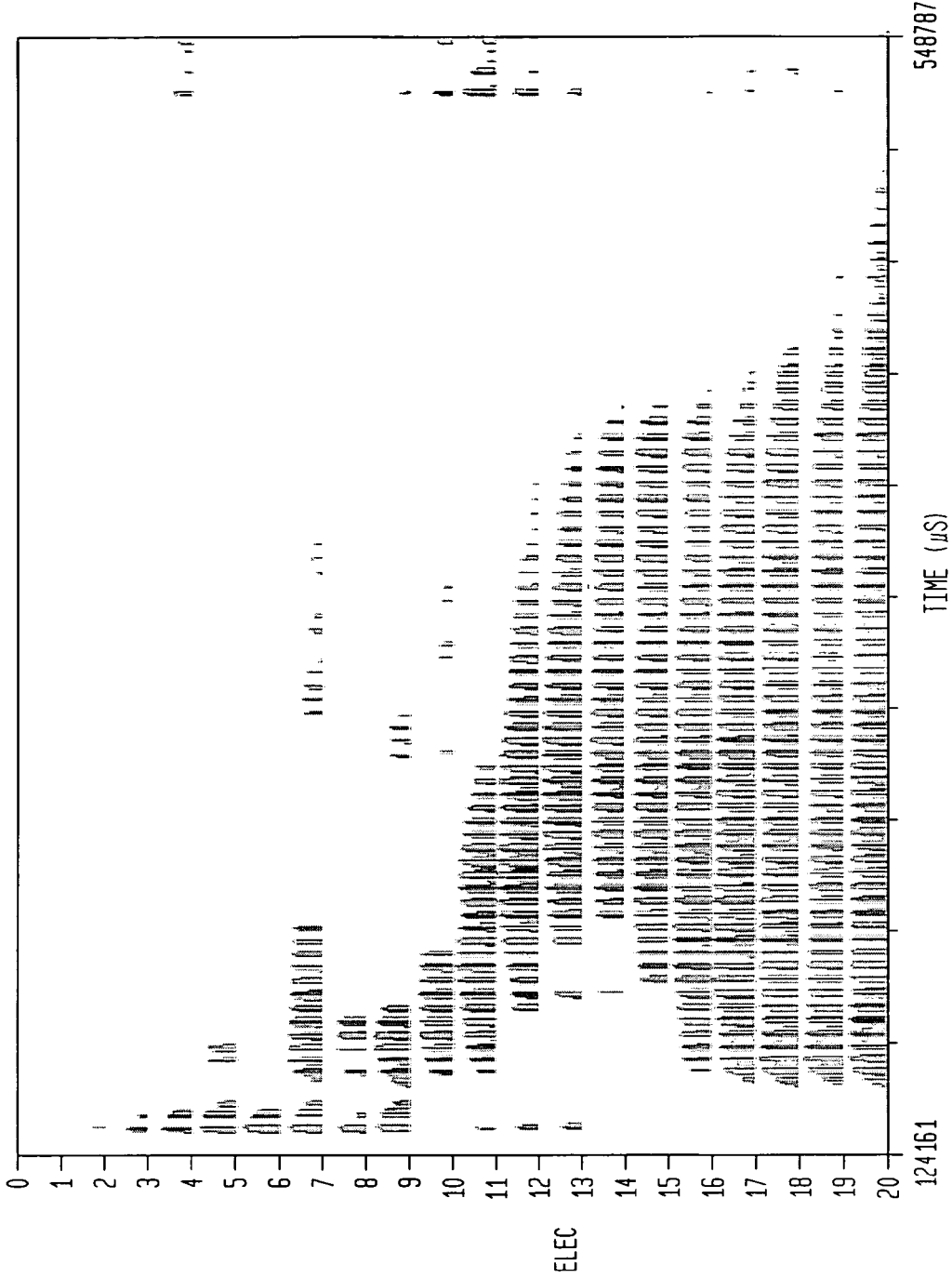
FIG. 25 is an electrodogram (stimulus output pattern) of sound signals to show the overall effect of the implementation of one embodiment of the present invention.

To illustrate the effect of the MEM strategy on the coding of speech signals, stimulus output patterns, known as electrodograms (which are similar to spectrograms for acoustic signals), which plot stimulus intensity (plotted as log current level) for each electrode (channel) as a function of time, were recorded for the ACE and MEM strategies and are shown in FIGS. 23 through 25. The speech token presented in these recordings was "dog" and was spoken by a female speaker having a fundamental voicing frequency of approximately 190 Hz. FIG. 23 displays the electrodogram for the ACE strategy. FIGS. 24 and 25 display electrodograms for the MEM strategy employing a scaling factor (Env K) of 4 and 1, respectively.

It will therefore be understood that the net outcome is to substantially impose the modulation information from the modified broadband envelope signal onto all the channels, with the retained information being largely relative signal amplitudes. As a consequence, modulation in the envelopes of all the narrow band signals will be in phase, and in general will have increased modulation depth.

It should be appreciated that the MEM strategy of this aspect of the invention may be applied to the channelized sound signal, and subsequent processing may continue as per any selected processing strategy for cochlear implants. This strategy is specific to this stage of processing, and hence is applicable to any strategy which employs channelization and subsequent processing (with modifications as may be dictated by the requirements of the selected strategy).

It should also be appreciated that there are numerous alternate embodiments of this aspect of the invention which are considered within the scope of the present invention. What follows is a brief discussion of several of these alternate embodiments. Since modifications within the spirit and scope of the invention may be readily effected by persons skilled in the art, it is to be understood that the invention is not limited to the particular embodiment described by way of example. Some of these modifications are described below.

Figure 26:
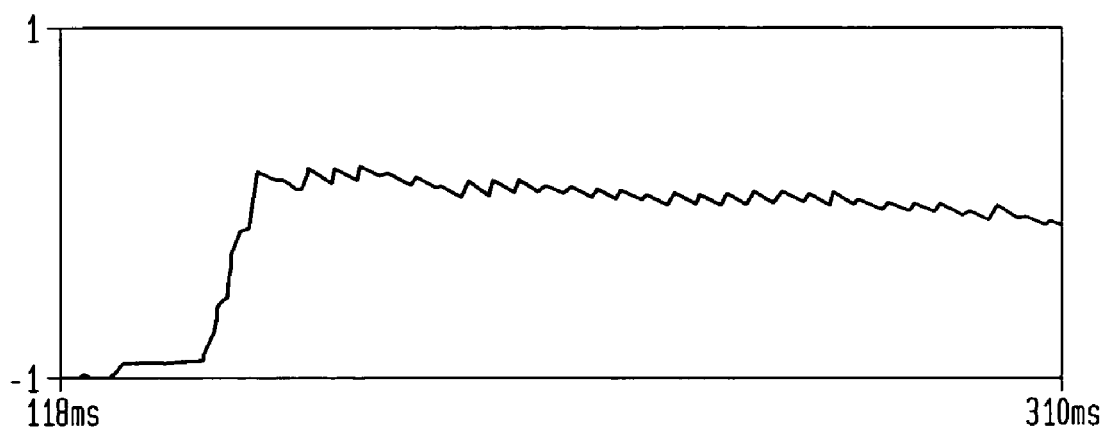
FIG. 26 depicts a signal waveform at various locations in the signal processing path for an alternative embodiment of the present invention.
Figure 27:
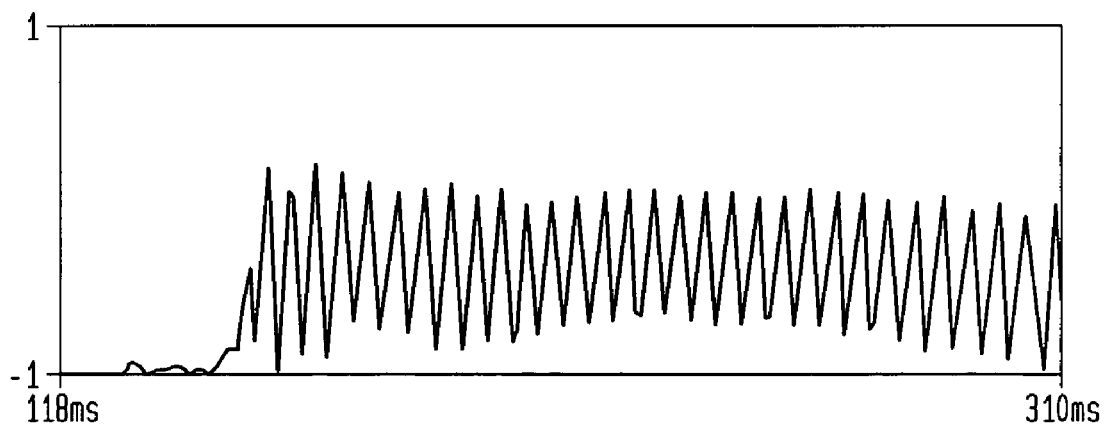
FIG. 27 depicts a signal waveform at various locations in the signal processing path for an alternative embodiment of the present invention.

Different methods could be employed in low pass filters 1308 to smooth the narrow-band channel signals derived from band-pass filter bank 204. For instance, low-pass filter 1308 could be replaced by an envelope tracker that follows peaks in the signal (i.e. instantaneous attack time), holds peak signal levels (or uses a slow release time) for a period of approximately 12 ms (to smooth frequency components above approximately 80 Hz) after which a rapid release time constant is then applied. Using the example narrow-band channel signal shown in FIG. 20, the output of this peak envelope tracker is shown in FIG. 26 and the modulated channel output in FIG. 27.

The low-pass filter 1318 used to estimate the broadband envelope signal can be reduced in its cut-off frequency so that the unwanted affect of higher order harmonics in the envelope when F0 is low (e.g. below 150 Hz) can be minimized. Often, the higher order harmonics of the fundamental F0 can be greater in intensity than the fundamental and as such they will introduce secondary or higher order peaks in the temporal envelope that can disrupt the desired F0 periodicity waveform. By attenuating these harmonics there is less chance of this arising. In addition, because the envelope signal is normalized in the final stage of processing, attenuation of F0 in cases when it is higher than the low-pass filter cut-off is not a problem, provided that the system has sufficient numerical dynamic, and a low-noise floor.

Figure 28:
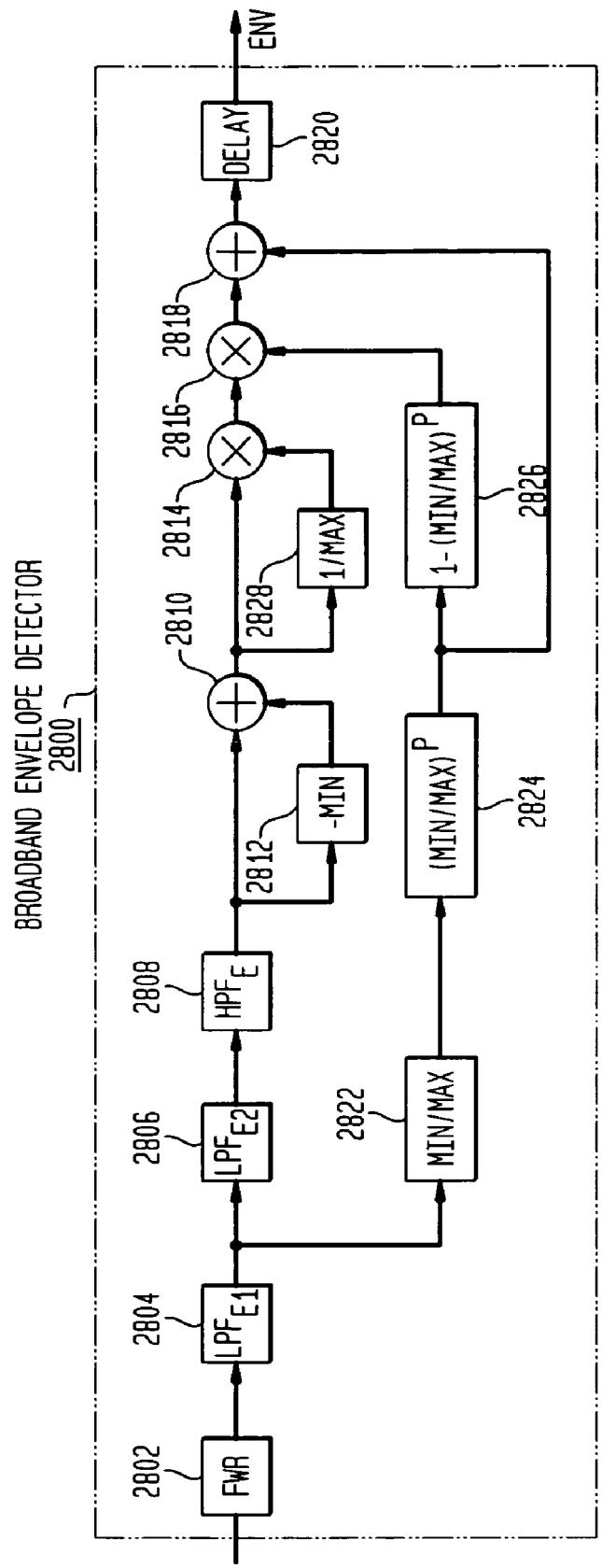
FIG. 28 depicts a schematic representation of an alternative embodiment of the invention.

Many techniques may be employed to derive the normalized broadband envelope signal which is used to modulate the narrow-band envelope signals. FIG. 28 is a schematic block diagram of an alternative embodiment of broadband envelope detector 1306, referred to herein as detector 2800. Broadband envelope detector 2800 comprises a full-wave rectifier 2802 that full-wave rectifies the broadband signal, a low-pass filter 2804 that filters the output of full-wave rectifier 2802 using, in this embodiment, a 300 Hz, $4^{th}$ order Butterworth, IIR LPF. The broadband envelope signal is further low-pass filtered at block 2806 using, in this embodiment, a 120 Hz, $2^{nd}$ order Butterworth, (IIR) LPF. The signal is then high-pass filtered at block 2808 using, in this embodiment, a 300 Hz, $2^{nd}$ order Butterworth IIR HPF.

This signal is then normalized (shifted and scaled) at adder 2810 such that peak (maximum) levels do not exceed 1.0 and trough (minimum) levels never fall below 0.0. This is achieved by adding the negative of the signal minimum generated at block 2812 (as determined over a finite time interval using a sliding time window of approximately 12 ms in duration) and scaling at multiplier 2814 the signal by the inverse of its maximum level (also determined using a sliding time window of approximately 12 ms in duration), as determined by block 2828.

Figure 29:
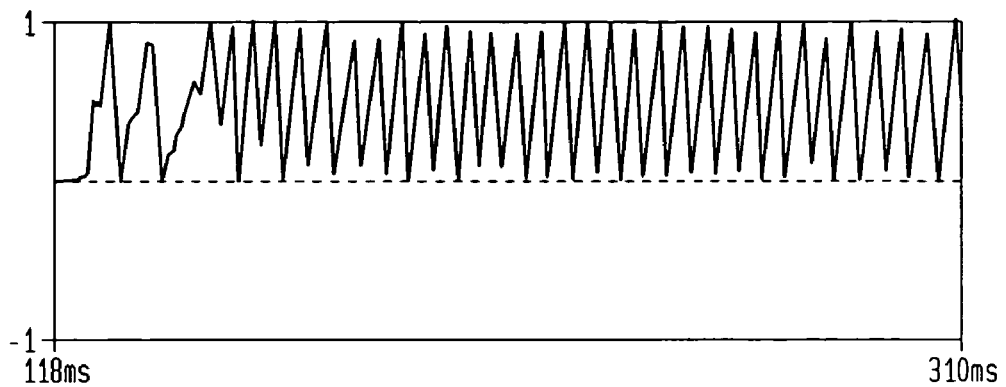
FIG. 29 depicts a signal waveform at various locations in the signal processing path for an alternative embodiment of the present invention.
Figure 30:
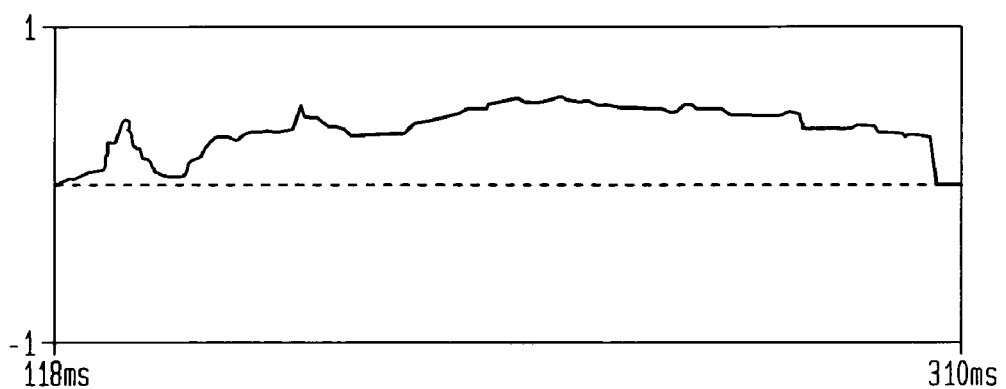
FIG. 30 depicts a signal waveform at various locations in the signal processing path for an alternative embodiment of the present invention.
Figure 31:
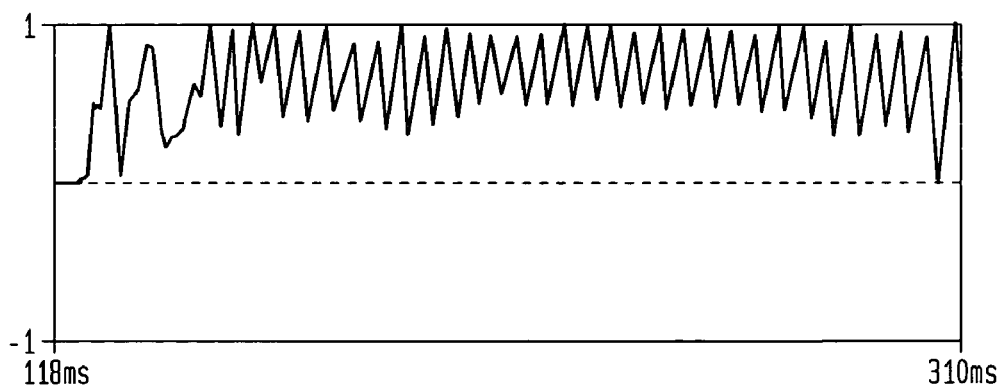
FIG. 31 depicts a signal waveform at various locations in the signal processing path for an alternative embodiment of the present invention.
Figure 33:
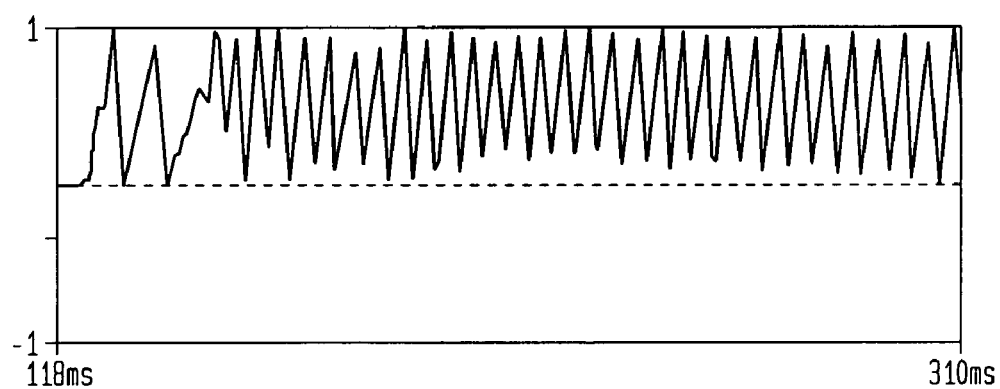
FIG. 33 depicts a signal waveform at various locations in the signal processing path for an alternative embodiment of the present invention.

FIG. 29 illustrates the normalized envelope signal for the example broadband signal shown in FIG. 14. The minimum level of the normalized envelope signal is then adjusted so that its trough-to-peak (Min/Max) ratio (or "inverse modulation depth") is proportional to a function of the trough-to-peak ratio of the broadband envelope signal. This is achieved by calculating the "inverse modulation depth" at block 2822 as shown in FIG. 30, which can be raised to some power (P) at block 2824. This is then used to scale at multiplier 2816 the normalized envelope signal by a factor of $[1-(Min/Max)^P]$ generated at block 2826 (where Min and Max are the peak and trough levels respectively of the broadband envelope signal as determined over a finite time interval using a sliding time window of approximately 12 ms in duration). The signal is then adjusted at adder 2818 by a factor of $(Min/Max)^P$ generated at block 2824 as noted above. P can be used to control the degree of modulation depth expansion to be applied to the signal. For example P=1 provides no expansion whereas P=3 expands the modulation depth by a power of 3. FIGS. 31 and 33 display the adjusted normalized envelope signals for P=1 and 3 respectively.

Figure 32:
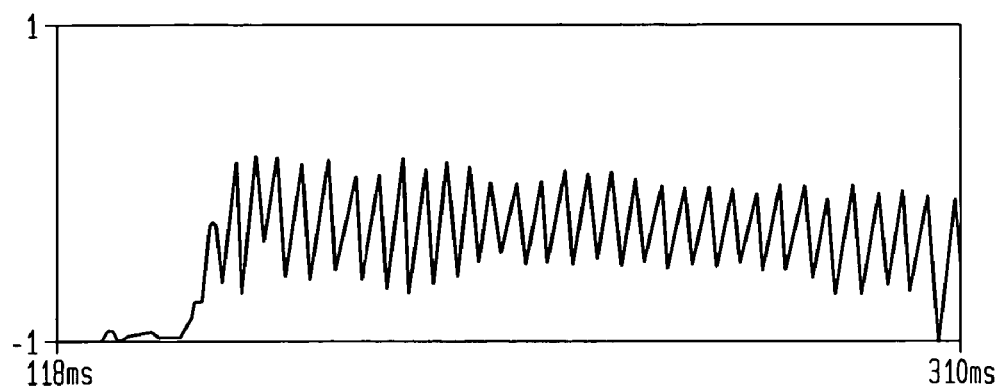
FIG. 32 depicts a signal waveform at various locations in the signal processing path for an alternative embodiment of the present invention.
Figure 34:
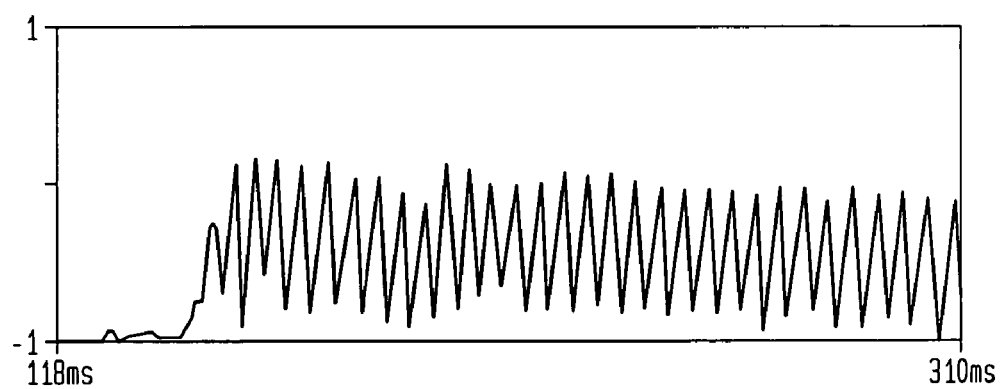
FIG. 34 depicts a signal waveform at various locations in the signal processing path for an alternative embodiment of the present invention.

Finally, the normalized envelope signal is delayed at block 2820 by approximately 6 ms and used to modulate the narrow-band envelope signals at channel modulation module 1304 derived from the N-channel filter bank 204 of the ACE strategy. FIGS. 32 through 34 display the modulated channel signals for P=1 and 3 for the example narrow-band channel signal depicted in FIG. 20.

It should be appreciated that other techniques for expansion of modulation depth, such as that described above in "Modulation Depth Enhancement," could also be sued to expand the modulation depth of the broadband envelope signal.

This aspect of the present invention is also not limited to use of a single broadband envelope detector 1306 or 2800 (derived from a frequency range of approximately 0 to 8 KHz) to modulate the narrow-band channel signals ($e_n$). Several broadband envelope signals may be measured in different spectral regions (e.g. 0 to 4 KHz and 4 to 8 KHz) by different broadband envelope detectors which could be used to modulate at module 1304 the smoothed narrow-band envelope signals derived from within those spectral regions specifically. For example, a first broadband envelope may relate to voiced regions, and a second to unvoiced regions. It is possible to use more than two regions in accordance with the present invention, however, this is not presently preferred. Inserting multiple broadband regions risks creating artificial boundaries between channel groups and which may affect perception of the modulation frequency and hence pitch by recipients.

F. References

Abberton, E., & Fourcin, A. (1978). "Intonation and speaker identification," Lang. Speech 21, 305-318.

Barry, J. G., P. J. Blamey, et al. (2002). "A multidimensional scaling analysis of tone discrimination ability in Cantonese-speaking children using a cochlear implant." Clin. Linguist. Phon. 16(2), 101-13.

Brokx, J. P. L., & Nooteboom, S. G. (1982). "Intonation and the perceptual separation of simultaneous voices," J. Phonetics, 10, 23-36.

Ciocca, V., Francis, A. L., Aisha, R., & Wong, L. (2002). "The perception of Contonese lexical tones by early-deafened cochlear implantees," J. Acoust. Soc. Am. 111, 2250-2256.

Highnam, C., & Morris, V. (1987). "Linguistic stress judgments of language learning disabled students," J. Commun. Disord. 20, 93-103.

Liberman, P., & Michaels, S. B. (1962). "Some aspects of fundamental frequency and envelope amplitude as related to the emotional content of speech," J. Acoust. Soc. Am. 34, 922-927.

Lee, K. Y. S., van Hasselt, C. A., Chiu, S. N., & Cheung, D. M. C. (2002). "Cantonese tone perception ability of cochlear implant children in comparison with normal-hearing children," Int. J. Ped. Otolaryngol. 63, 137-147.

Liberman, P., & Michaels, S. B. (1962). "Some aspects of fundamental frequency and envelope amplitude as related to the emotional content of speech," J. Acoust. Soc. Am. 34, 922-927.

McDermott, H. J., & Vandali, A. E. (1991). "Spectral Maxima Sound Processor," Australian Patent, 657959; U.S. Pat. No. 788,591.

McDermott, H. J., McKay, C. M. (1997). "Musical pitch perception with electrical stimulation of the cochlea," J. Acoust. Soc. Am. 101, 1622-1631.

McDermott, H. J., McKay, C. M., & Vandali, A. E. (1992). "A new portable sound processor for the University of Melbourne/Nucleus Limited multielectrode cochlear implant," J. Acoust. Soc. Am. 91, 3367-3371.

McKay, C. M., McDermott, H. J., & Clark, G. M (1994). "Pitch percepts associated with amplitude-modulated current pulse trains by cochlear implantees," J. Acoust. Soc. Am. 96, 2664-2673.

McKay, C. M., & McDermott, H. J. (1996). "The perception of temporal patterns for electrical stimulation presented at one or two intracochlear sites," J. Acoust. Soc. Am. 100, 1081-1092.

Moore, B. C. J. (1995). "Hearing" in The handbook of Perception and Cognition (2nd ed.), edited by B. C. J. Moore (Academic Press, Inc., London), pp 267-295.

Nooteboom, S. (1997). "The prosody of speech: Melody and rhythm," in The handbook of Phonetic Sciences, edited by W. J. Hardcastle and J. Layer (Blackwell, Oxford), pp 640-673.

Pijl, S. and D. W. Schwarz (1995). "Melody recognition and musical interval perception by deaf subjects stimulated with electrical pulse trains through single cochlear implant electrodes," J. Acoust. Soc. Am. 98, (2 Pt 1), 886-95.

Seligman, P. M., Dowell, R. C., Blamey, P. J. (1992). "Multi Peak Speech Procession," U.S. Pat. No. 5,095,904.

Skinner, M. W., Holden, L. K., Holden, T. A., Dowell, R. C., Seligman, P. M., Brimacombe, J. A., & Beiter, A. L. (1991). "Performance of postlinguistically deaf adults with the Wearable Speech Processor (WSP III) and the Mini Speech Processor (MSP) of the Nucleus multi-electrode cochlear implant," Ear and Hearing, 12, 3-22.

Skinner, M. W., Clark, G. M., Whitford, L. A., Seligman, P. A., Staller, S. J., Shipp, D. B., Shallop, J. K., Everingham, C., Menapace, C. M., Arndt, P. L., Antogenelli, T., Brimacombe, J. A., & Beiter, A. L. (1994). "Evaluation of a new spectral peak (SPEAK) coding strategy for the Nucleus 22 channel cochlear implant system," The Am. J. Otology, 15, (Suppl. 2), 15-27.

Skinner, M. W., Arndt, P. L., & Staller, S. J. (2002). "Nucleus 24 advanced encoder conversion study: Performance versus preference," Ear and Hearing, 23 (Suppl.), 2S-127S.

Vandali, A. E., Whitford, L. A., Plant, K. L., & Clark, G. M. (2000). "Speech perception as a function of electrical stimulation rate: Using the Nucleus 24 Cochlear implant system," Ear & Hearing, 21, 608-624.

Vandali, A. E., Sucher, C., Tsang, D. J., McKay, C. M., McDermott, H. J., (May, 2005). "Pitch Ranking Ability of Cochlear Impant Recipients: A Comparison of Sound Processing Strategies," J. Acoust. Soc. Am. 117 (5), 3126-3138.

Wells, B., Peppe, S., & Vance, M. (1995). "Linguistic assessment of prosody," in Linguistics in Clinical Practice, edited by K. Grundy (Whurr, London), pp 234-265.

Whitford, L. A., Seligman, P. M., Everingham, C. E., Antognelli, T., Skok, M. C., Hollow, R. D., Plant, K. L., Gerin, E. S., Staller, S. J., McDermott, H. J., Gibson, W. R., Clark, G. M. (1995). "Evaluation of the Nucleus Spectra 22 processor and new speech processing strategy (SPEAK) in post-linguistically deafened adults," Acta Oto-laryngologica (Stockholm), 115, 629-637.

Wilson, B. S., Finley, C. C., Lawson, D. T., Wolford, R. D., Eddington, D. K., & Rabinowitz, W. M. (1991). "Better speech recognition with cochlear implants," Nature, 352, 236-238.

G. Closing

All documents, patents, journal articles and other materials cited in the present application are hereby incorporated by reference herein. Furthermore, the present application is a continuation-in-part application of U.S. patent application Ser. No. 11/025,930 filed Jan. 3, 2005 entitled "Modulation Depth Enhancement for Tone Perception, naming as inventors Andrew Vandali and Richard Van Hoesel. U.S. patent application Ser. No. 11/025,930 claims priority from Australian Provisional Patent Application 2003907206, filed Dec. 31, 2003, entitled "Modulation Depth Enhancement For Tone Perception," and naming as inventors Andrew Vandali and Richard Van Hoesel. The present invention also claims priority from U.S. Provisional Patent Application 60/613,230, filed Sep. 28, 2004, entitled "Phase Alignment of Amplitude Sound Signals," naming as inventors Andrew Vandali and Richard Van Hoesel. The present invention claims priority from U.S. Provisional Patent Application 60/613,229, filed Sep. 28, 2004, entitled "Multi-Channel Envelope Modulation," naming as inventors Andrew Vandali, Richard Van Hoesel, and Peter Seligman. These applications are hereby incorporated by reference herein in their entirety.

It should be appreciated that the above embodiments may be combined with each other in any manner feasible. For example, the inventors have observed the best results in temporal pitch perception have been obtained when embodiments of the modulation depth enhancement aspect of the present invention are combined with embodiments of the phase alignment aspect of the present invention strategy to align temporal peaks across channels.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for processing a sound signal having a fundamental frequency, the method comprising:
processing the sound signal to produce channel signals in spaced frequency channels;
determining an envelope signal for each of a plurality of the channel signals; and
modulating the envelope signals in each channel with at least one broadband envelope signal derived from the input sound signal, such that the phase of modulated signals in the narrow band channels are synchronized.

2. The method of claim 1, wherein the at least one broadband envelope signal contains modulation information related to the fundamental frequency of the sound signal, and wherein the modulated envelope signals contain the modulation information.

3. The method of claim 1, wherein the broadband envelope signal has a modulation depth, and wherein the method further comprises:
increasing the modulation depth of the broadband envelope signal prior to modulating the envelope signals.

4. The method of claim 3, wherein increasing the modulation depth of the broadband envelope comprises:
increasing the modulation depth of the broadband envelope signal such that the average modulation depth in each channel is increased.

5. The method of claim 3, wherein increasing the modulation depth of the broadband envelope signal comprises:
transforming the broadband envelope signal with a function so as to increase the modulation depth of periodic terms in the broadband envelope signal.

6. The method of claim 1, further comprising:
performing additional sound processing operations on the modulated envelope signals and any remaining channel signals.

7. The method of claim 1, further comprising:
modifying the channel signals to substantially remove amplitude modulation in the channel signals, prior to modulating the envelope signals with a broadband envelope signal.

8. The method of claim 1, further comprising:
normalizing the broadband envelope signal prior to modulating the envelope signals with a broadband envelope signal.

9. The method of claim 1, wherein modulating the envelope signals with at least one broadband envelope signal comprises
modulating the envelope signals with a plurality of broadband envelope signals derived from the received sound signal, each broadband envelope signal corresponding to different frequency regions of the received sound signal, and wherein each broadband envelope signal is used to modulate the level of channel signals derived within its respective frequency region.

10. An auditory prosthesis for generating a therapeutic output representative of a received sound signal, comprising:
a speech processing unit configured to process the sound signal to produce channel signals in spaced frequency channels; to determine an envelope signal for each of a plurality of the channel signals; and to modulate the envelope signals with at least one broadband envelope signal containing modulation information related to the fundamental frequency of the sound signal such that the modulated envelope signals have synchronized phases and contain the modulation information related to the fundamental frequency of the sound signal.

11. The auditory prosthesis of claim 10, wherein the speech processor comprises:
- a filter bank configured to process the sound signal to generate envelope signals in each of a plurality of spaced frequency channels;
- a broadband envelope detector configured to measure the envelope of at least one broadband signal; and
- a channel modulation module that uses the at least one broadband envelope signal to modulate the channel envelope signals to generate modulated envelope signals.

12. The auditory prosthesis of claim 10, wherein the auditory prosthesis comprises a cochlear implant system.

13. A speech processing unit for processing a sound signal, comprising: means for processing the sound signal to produce channel signals in spaced frequency channels;
- means for determining an envelope signal for each of a plurality of the channel signals; and
- means for modulating the envelope signals with at least one broadband envelope signal containing modulation information related to the fundamental frequency of the sound signal such that the modulated envelope signals have synchronized phases and contain the modulation information.

14. The speech processing unit of claim 13, where the received sound signal is a voiced signal, and further wherein the fundamental frequency of the input sound signal is a voicing frequency.

15. The speech processing unit of claim 13, wherein the broadband envelope signal has a modulation depth, and wherein the method further comprises:
- means for increasing the modulation depth of the broadband envelope signal prior to modulating the envelope signals.

* * * * *